(12) United States Patent
Khanna

(10) Patent No.: US 7,976,845 B2
(45) Date of Patent: Jul. 12, 2011

(54) HUMAN CYTOMEGALOVIRUS IMMUNOTHERAPY

(75) Inventor: Rajiv Khanna, Herston (AU)

(73) Assignee: The Council of the Queensland Institute of Medical Research, Herston, Queensland (AU)

( * ) Notice: Subject to any disclaimer, the term of this patent is extended or adjusted under 35 U.S.C. 154(b) by 316 days.

(21) Appl. No.: 11/720,421

(22) PCT Filed: Nov. 29, 2005

(86) PCT No.: PCT/AU2005/001798
§ 371 (c)(1),
(2), (4) Date: Nov. 1, 2007

(87) PCT Pub. No.: WO2006/056027
PCT Pub. Date: Jun. 1, 2006

(65) Prior Publication Data
US 2008/0107620 A1    May 8, 2008

(30) Foreign Application Priority Data
Nov. 29, 2004  (AU) ................................ 2004906783

(51) Int. Cl.
*A61K 39/245* (2006.01)
*A61K 39/295* (2006.01)
*C07K 19/00* (2006.01)
*C07K 14/045* (2006.01)
*C12N 15/62* (2006.01)
*C12N 15/38* (2006.01)

(52) U.S. Cl. .................. 424/192.1; 424/230.1; 530/350; 435/235.1; 536/23.72; 536/23.4

(58) Field of Classification Search .................. None
See application file for complete search history.

(56) References Cited

FOREIGN PATENT DOCUMENTS

| WO | WO 03/000720 | * | 1/2003 |
|----|--------------|---|--------|
| WO | WO 03/000720 A1 | | 1/2003 |
| WO | WO 2004/007556 | * | 1/2004 |

OTHER PUBLICATIONS

Carlson et al. "Expression, Purification, and Characterization of a Soluble Form of human Cytomegalovirus Glycoprotein B." Virology 239:198-205, 1997.*
Beninga et al (Journal of General Virology 76:153-160, 1995).*
Fields et al (Fields Virology, Third Edition, vol. 2, pp. 2376, 2456; Lippincott Williams & Wilkins, Philadelphia; 1996).*
Tanner et al (Journal of Virology 62:4452-4464, 1998).*
Strive et al (Journal of Virology 76: 1252-1264, 2002).*
Carlson et al (Virology 239:198-205, 1997).*
Chou, S et al. 1992 "Comparative analysis of sequence variation in gp116 and gp55 components of glycoprotein B of human cytomegalovirus" *Virology* 188:388-390.
Rist, M et al. 2005 "Ex vivo expansion of human cytomegalovirus-specific cytotoxic T cells by recombinant polyepitope: implications for HCMV immunotherapy" *Eur J Immunol* 35:996-1007.
Spaete, R.R. et al. 1988 "Human cytomegalovirus strain Towne glycoprotein B is processed by proteolytic cleavage" *Virology* 167:207-225.

* cited by examiner

*Primary Examiner* — Mary E Mosher
(74) *Attorney, Agent, or Firm* — Knobbe Martens Olson & Bear LLP

(57) ABSTRACT

An isolated protein construct comprising a polyepitope derived from multiple human cytomegalovirus protein antigen epitopes conjugated to an extracellular domain of glycoprotein B, which isolated protein is capable of eliciting a cytotoxic T-lymphocyte immune response as well as a neutralizing antibody response to human cytomegalovirus. Also provided are pharmaceutical compositions comprising the isolated protein or an adenoviral expression construct for delivery and expression of a nucleic acid encoding the isolated protein for prophylactic and/or therapeutic treatment of human cytomegalovirus infection, particularly in humans.

10 Claims, 15 Drawing Sheets

Figure 1:
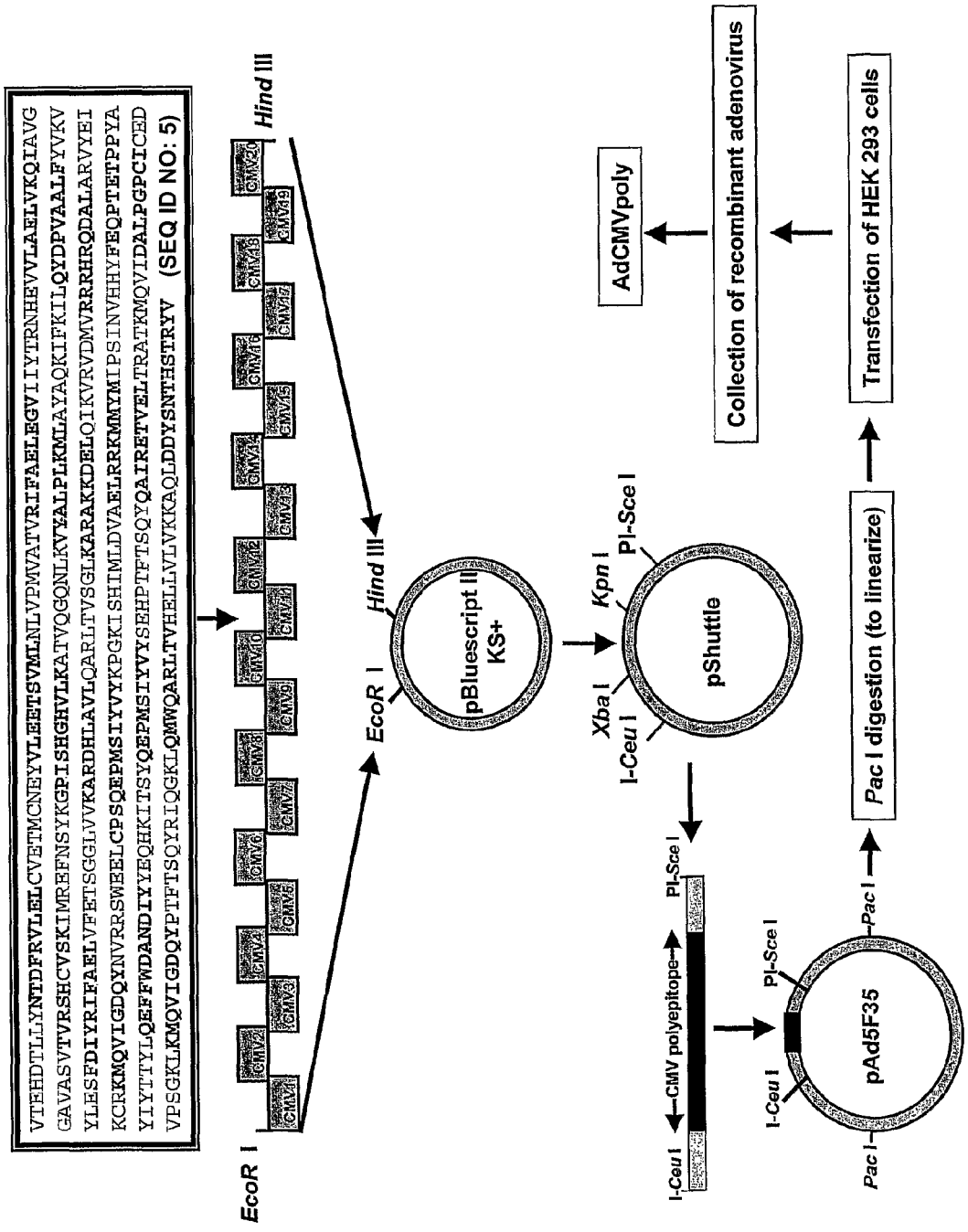

```
MESRIWCLVVCVNLCIVCLGAAVSSSSTSHATSSTHNGSHTSRTTSA
QTRSVYSQHVTSSEAVSHRANETIYNTTLKYGDVVGVNTTKYPYRVC
SMAQGTDLIRFERNIICTSMKPINEDLDEGIMVVYKRNIVAHTFKVR
VYQKVLTFRRSYAYIYTTYLLGSNTEYVAPPMWEIHHINKFAQCYSS
YSRVIGGTVFVAYHRDSYENKTMQLIPDDYSNTHSTRYVTVKDQWHS
RGSTWLYRETCNLCMLTITTARSKYPYHFFATSTGDVVYISPFYNG
TNRNASYFGENADKFFIFPNYTIVSDFGRPNAAPETHRLVAFLERAD
SVISWDIQDEKNVTCQLTFWEASERTIRSEAEDSYHFSSAKMTATFL
SKKQEVNMSDSALDCVRDEAINKLQQIFNTSYNQTYEKYGNVSVFET
SGGLVVFWQGIKQKSLVELERLANRSSLNITHRTRRSTSDNNTTHLS
SMESVHNLVYAQLQFTYDTLRGYINRALAQIAEAWCVDQRRTLEVFK
ELSKINPSAILSAIYNKPIAARFMGDVLGLASCVTINQTSVKVLRDM
NVKESPGRCYSRPVVIFNFANSSYVQYGQLGEDNEILLGNHRTEECQ
LPSLKIFIAGNSAYEYVDYLFKRMIDLSSISTVDSMIALDIDPLENT
DFRVLELYSQKELRSSNVFDLEEIMREFNSYKQRVKYVEDKVVTEHD
TLLYKPGKISHIMLDVANTDFRVLELVLEETSVMLNLVPMVATVRIF
AELEGVIIYTRNHEVCVETMCNEYVLAELVKQIAVGGAVASVTVRSH
CVSKIMREFNSYKGPISHGHVLKAYAQKIFKILQYDPVAALFYVKVY
LESFDIYRIFAELVFETSGGLVVKARDHLAVLKARAKKDELTRATKM
QVIHELLVLVKKAQLDDYSNTHSTRYVQIKVRVDMVRRRHRQDALAR
VYEIKCRNVRRSWEELCPSQEPMSIYVYQARLTVSGLELRRKMMYMI
PSINVHHYFEQPTETPPYAYIYTTYLQEFFWDANDIYYEQHKITSYQ
EPMSIYVYSEHPTFTSQYQAIRETVELCEDVPSGKLKMQVIGDQYAT
VQGQNLKHERNGFTVLDALPGPCIVYALPLKMLPTFTSQYRIQGKLQ
MWQARLTV (SEQ ID NO: 1)
```

*FIG. 11A*

```
   1  atggaatcca ggatctggtg cctggtagtc tgcgttaacc tgtgtatcgt
  51  ctgtctgggt gctgcggttt cctcttctag tacttcccat gcaacttctt
 101  ctactcacaa tggaagccat acttctcgta cgacgtctgc tcaaacccgg
 151  tcagtctatt ctcaacacgt aacgtcttct gaagccgtca gtcatagagc
 201  caacgagact atctacaaca ctaccctcaa gtacggagat gtggtgggag
 251  tcaacactac caagtacccc tatcgcgtgt gttctatggc ccagggtacg
 301  gatcttattc gctttgaacg taatatcatc tgcacctcga tgaagcctat
 351  caatgaagac ttggatgagg gcatcatggt ggtctacaag cgcaacatcg
 401  tggcgcacac ctttaaggta cgggtctacc aaaaggtttt gacgtttcgt
 451  cgtagctacg cttacatcta caccacttat ctgctgggca gcaatacgga
 501  atacgtggcg cctcctatgt gggagattca tcacatcaac aagtttgctc
 551  aatgctacag ttcctacagc cgcgttatag gaggcacggt tttcgtggca
 601  tatcataggg acagttatga aaacaaaacc atgcaattaa ttcccgacga
 651  ttattccaac acccacagta cccgttacgt gacggtcaag gatcagtggc
 701  acagccgcgg cagcacctgg ctctatcgtg agacctgtaa tctgaactgt
 751  atgctgacca tcactactgc gcgctccaag tatccttatc attttttttgc
 801  aacttccacg ggtgatgtgg tttacatttc tcctttctac aacggaacca
 851  atcgcaatgc cagctacttt ggagaaaacg ccgacaagtt tttcattttc
 901  ccgaactaca ccatcgtttc cgactttgga agacccaacg ctgcgccaga
 951  aacccatagg ttggtggctt ttctcgaacg tgccgactcg gtgatctctt
1001  gggatataca ggacgagaag aatgtcacct gccagctcac cttctgggaa
1051  gcctcggaac gtactatccg ttccgaagcc gaagactcgt accactttttc
1101  ttctgccaaa atgactgcaa cttttctgtc taagaaacaa gaagtgaaca
1151  tgtccgactc cgcgctggac tgcgtacgtg atgaggctat aaataagtta
1201  cagcagattt tcaatacttc atacaatcaa acatatgaaa aatacggaaa
1251  cgtgtccgtc ttcgaaacca gcggcggtct ggtggtgttc tggcaaggca
1301  tcaagcaaaa atctttggtg gaattggaac gtttggccaa tcgatccagt
1351  ctgaatatca ctcataggac cagaagaagt acgagtgaca ataatacaac
1401  tcatttgtcc agcatggaat cggtgcacaa tctggtctac gcccagctgc
1451  agttcaccta tgacacgttg cgcggttaca tcaaccgggc gctggcgcaa
1501  atcgcagaag cctggtgtgt ggatcaacgg cgcaccctag aggtcttcaa
1551  ggaactcagc aagatcaacc cgtcagccat tctctcggcc atttacaaca
1601  aaccgattgc cgcgcgtttc atgggtgatg tcttgggcct ggccagctgc
1651  gtgaccatca accaaaccag cgtcaaggtg ctgcgtgata tgaacgtgaa
1701  ggaatcgcca ggacgctgct actcacgacc cgtggtcatc tttaatttcg
1751  ccaacagctc gtacgtgcag tacggtcaac tgggcgagga caacgaaatc
1801  ctgttgggca accaccgcac tgaggaatgt cagcttccca gcctcaagat
1851  cttcatcgcc gggaactcgg cctacgagta cgtggactac ctcttcaaac
1901  gcatgattga cctcagcagt atctccaccg tcgacagcat gatcgccctg
1951  gatatcgacc cgctggaaaa taccgacttc agggtactgg aactttactc
2001  gcagaaagag ctgcgttcca gcaacgtttt tgacctcgaa gagatcatgc
2051  gcgaattcaa ctcgtacaag cagcgggtaa agtacgtgga ggacaaggta
2101  aagcttGTGA CCGAGCACGA CACCCTGCTG TACAAGCCCG GCAAGATCAG
2151  CCACATCATG CTGGACGTGG CCAACACCGA CTTCCGCGTG CTGGAGCTGG
2201  TGCTGGAGGA GACCAGCGTG ATGCTGAACC TGGTGCCCAT GGTGGCCACC
2251  GTGCGCATCT TCGCCGAGCT GGAGGGCGTG ATCATCTACA CCCGCAACCA
2301  CGAGGTGTGC GTGGAGACCA TGTGCAACGA GTACGTGCTG GCCGAGCTGG
2351  TGAAGCAGAT CGCCGTGGGC GGCGCCGTGG CCAGCGTGAC CGTGCGCAGC
2401  CACTGCGTGA GCAAGATCAT GCGCGAGTTC AACAGCTACA AGGGCCCCAT
2451  CAGCCACGGC CACGTGCTGA AGGCCTACGC CCAGAAGATC TTCAAGATCC
2501  TGCAGTACGA CCCCGTGGCC GCCCTGTTCT ACGTGAAGGT GTACCTGGAG
2551  AGCTTCGACA TCTACCGCAT CTTCGCCGAG CTGGTGTTCG AGACCAGCGG
2601  CGGCCTGGTG GTGAAGGCCC GCGACCACCT GGCCGTGCTG AAGGCCCGCG
2651  CCAAGAAGGA CGAGCTGACC CGCGCCACCA AGATGCAGGT GATCCACGAG
2701  CTGCTGGTGC TGGTGAAGAA GGCCCAGCTG GACGACTACA GCAACACCCA
2751  CAGCACCCGC TACGTGCAGA TCAAGGTGCG CGTGGACATG GTGCGCCGCC
2801  GCCACCGCCA GGACGCCCTG GCCCGCGTGT ACGAGATCAA GTGCCGCAAC
2851  GTCGCCGCA GCTGGGAGGA GCTGTGCCCC AGCCAGGAGC CCATGAGCAT
2901  CTACGTGTAC CAGGCCCGCC TGACCGTGAG CGGCCTGGAG CTGCGCCGCA
```

*FIG. 11B*

```
2951  AGATGATGTA CATGATCCCC AGCATCAACG TGCACCACTA CTTCGAGCAG
3001  CCCACCGAGA CCCCCCCCTA CGCCTACATC TACACCACCT ACCTGCAGGA
3051  GTTCTTCTGG GACGCCAACG ACATCTACTA CGAGCAGCAC AAGATCACCA
3101  GCTACCAGGA GCCCATGAGC ATCTACGTGT ACAGCGAGCA CCCCACCTTC
3151  ACCAGCCAGT ACCAGGCCAT CCGCGAGACC GTGGAGCTGA AGCTTATCGA
3201  TTGCGAGGAC GTGCCCAGCG GCAAGCTGAA GATGCAGGTG ATCGGCGACC
3251  AGTACGCCAC CGTGCAGGGC CAGAACCTGA AGCACGAGCG CAACGGCTTC
3301  ACCGTGCTGG ACGCCCTGCC CGGCCCCTGC ATCGTGTACG CCCTGCCCCT
3351  GAAGATGCTG CCCACCTTCA CCAGCCAGTA CCGCATCCAG GGCAAGCTGC
3401  AGATGTGGCA GGCCCGCCTG ACCGTG (SEQ ID NO: 3)
```

*FIG. 11B cont'd*

```
GTAATMDAMKRGLCCVLLLCGAVFVSPSQEIHARFRRGARASSSTSHATSSTHNGSHTSR
TTSAQTRSVYSQHVTSSEAVSHRANETIYNTTLKYGDVVGVNTTKYPYRVCSMAQGTDLI
RFERNIICTSMKPINEDLDEGIMVVYKRNIVAHTFKVRVYQKVLTFRRSYAYIYTTYLLG
SNTEYVAPPMWEIHHINKFAQCYSSYSRVIGGTVFVAYHRDSYENKTMQLIPDDYSNTHS
TRYVTVKDQWHSRGSTWLYRETCNLNCMLTITTARSKYPYHFFATSTGDVVYISPFYNGT
NRNASYFGENADKFFIFPNYTIVSDFGRPNAAPETHRLVAFLERADSVISWDIQDEKNVT
CQLTFWEASERTIRSEAEDSYHFSSAKMTATFLSKKQEVNMSDSALDCVRDEAINKLQQI
FNTSYNQTYEKYGNVSVFETSGGLVVFWQGIKQKSLVELERLANRSSLNITHRTRRSTSD
NNTTHLSSMESVHNLVYAQLQFTYDTLRGYINRALAQIAEAWCVDQRRTLEVFKELSKIN
PSAILSAIYNKPIAARFMGDVLGLASCVTINQTSVKVLRDMNVKESPGRCYSRPVVIFNF
ANSSYVQYGQLGEDNEILLGNHRTEECQLPSLKIFIAGNSAYEYVDYLFKRMIDLSSIST
VDSMIALDIDPLENTDFRVLELYSQKELRSSNVFDLEEIMREFNSYKQRVKYVEDKVKLC
TQPLQNLFPYLVSADGTTVTSGSTKDTSLQAPPSYEESVYNSGRKGPGPPSSDASTAAPP
YTNEQAYQMLLALARLDAEQRAQQNGTDSLDGQTGTQDKGQKPNLLDRLRHRKNGYRHLK
DSDEEENVAAAVTEHDTLLYKPGKISHIMLDVANTDFRVLELVLEETSVMLNLVPMVATV
RIFAELEGVIIYTRNHEVCVETMCNEYVLAELVKQIAVGGAVASVTVRSHCVSKIMREFN
SYKGPISHGHVLKAYAQKIFKILQYDPVAALFYVKVYLESFDIYRIFAELVFETSGGLVV
KARDHLAVLKARAKKDELTRATKMQVIHELLVLVKKAQLDDYSNTHSTRYVQIKVRVDMV
RRRHRQDALARVYEIKCRNVRRSWEELCPSQEPMSIYVYQARLTVSGLELRRKMMYMIPS
INVHHYFEQPTETPPYAYIYTTYLQEFFWDANDIYYEQHKITSYQEPMSIYVYSEHPTFT
SQYQAIRETVELKLIDCEDVPSGKLKMQVIGDQYATVQGQNLKHERNGFTVLDALPGPCI
VYALPLKMLPTFTSQYRIQGKLQMWQARLTVHHHHHH*LE (SEQ ID NO: 2)
```

*FIG. 12A*

```
   1 GGTACCgccg ccaccatgga tgcaatgaag agagggctct gctgtgtgct
  51 gctgctgtgt ggagcagtct tcgtttcgcc cagccaggaa atccatgccc
 101 gattcagaag aggcgccaga GCTAGCtcta gtacttccca tgcaacttct
 151 tctactcaca atggaagcca tacttctcgt acgacgtctg ctcaaacccg
 201 gtcagtctat tctcaacacg taacgtcttc tgaagccgtc agtcatagag
 251 ccaacgagac tatctacaac actaccctca agtacggaga tgtggtggga
 301 gtcaacacta ccaagtaccc ctatcgcgtg tgttctatgg cccagggtac
 351 ggatcttatt cgctttgaac gtaatatcat ctgcacctcg atgaagccta
 401 tcaatgaaga cttggatgag ggcatcatgg tggtctacaa gcgcaacatc
 451 gtggcgcaca cctttaaggt acgggtctac caaaaggttt tgacgtttcg
 501 tcgtagctac gcttacatct acaccactta tctgctgggc agcaatacgg
 551 aatacgtggc gcctcctatg tgggagattc atcacatcaa caagtttgct
 601 caatgctaca gttcctacag ccgcgttata ggaggcacgg ttttcgtggc
 651 atatcatagg gacagttatg aaaacaaaac catgcaatta attcccgacg
 701 attattccaa cacccacagt acccgttacg tgacggtcaa ggatcagtgg
 751 cacagccgcg gcagcacctg gctctatcgt gagacctgta atctgaactg
 801 tatgctgacc atcactactg cgcgctccaa gtatccttat catttttttg
 851 caacttccac gggtgatgtg gtttacattt ctcctttcta caacggaacc
 901 aatcgcaatg ccagctactt ggagaaaaac gccgacaagt ttttcatttt
 951 cccgaactac accatcgttt ccgactttgg aagacccaac gctgcgccag
1001 aaacccatag gttggtggct tttctcgaac gtgccgactc ggtgatctct
1051 tgggatatac aggacgagaa gaatgtcacc tgccagctca ccttctggga
1101 agcctcggaa cgtactatcc gttccgaagc cgaagactcg taccacttt
1151 cttctgccaa aatgactgca acttttctgt ctaagaaaca agaagtgaac
1201 atgtccgact ccgcgctgga ctgcgtacgt gatgaggcta taaataagtt
1251 acagcagatt ttcaatactt catacaatca aacatatgaa aaatacggaa
1301 acgtgtccgt cttcgaaacc agcggcggtc tggtggtgtt ctggcaaggc
1351 atcaagcaaa aatctttggt ggaattggaa cgtttggcca atcgatccag
1401 tctgaatatc actcatagga ccagaagaag tacgagtgac aataatacaa
1451 ctcatttgtc cagcatggaa tcggtgcaca atctggtcta cgcccagctg
1501 cagttcacct atgacacgtt gcgcggttac atcaaccggg cgctggcgca
1551 aatcgcagaa gcctggtgtg tggatcaacg gcgcaccta gaggtcttca
1601 aggaactcag caagatcaac ccgtcagcca ttctctcggc catttacaac
1651 aaaccgattg ccgcgcgttt catgggtgat gtcttgggcc tggccagctg
1701 cgtgaccatc aaccaaacca gcgtcaaggt gctgcgtgat atgaacgtga
1751 aggaatcgcc aggacgctgc tactcacgac ccgtggtcat ctttaatttc
1801 gccaacagct cgtacgtgca gtacggtcaa ctgggcgagg acaacgaaat
1851 cctgttgggc aaccaccgca ctgaggaatg tcagcttccc agcctcaaga
1901 tcttcatcgc cgggaactcg gcctacgagt acgtggacta cctcttcaaa
1951 cgcatgattg acctcagcag tatctccacc gtcgacagca tgatcgccct
2001 ggatatcgac ccgctggaaa ataccgactt cagggtactg aactttact
2051 cgcagaaaga gctgcgttcc agcaacgttt tgacctcga agagatcatg
2101 cgcgaattca actcgtacaa gcagcgggta agtacgtgg aggacaaggt
2151 aAAGCTTtgc acgcagccgc tgcagaacct ctttccctat ctggtgtccg
2201 ccgacgggac caccgtgacg tcgggcagca ccaaagacac gtcgttacag
2251 gctccgcctt cctacgagga aagtgtttat aattctggtc gcaaaggacc
2301 gggaccaccg tcgtctgatg catccacggc ggctccgcct tacaccaacg
2351 agcaggctta ccagatgctt ctggccctgg ccgtctgga cgcagagcag
2401 cgagcgcagc agaacggtac agattctttg gacggacaga ctggcacgca
2451 ggacaaggga cagaagccta acctgctaga ccggctgcga atcgcaaaa
2501 acggctacag acacttgaaa gactccgacg aagaagagaa cgtcGcggcc
2551 gCGGTGACCG AGCACGACAC CCTGCTGTAC AAGCCCGGCA AGATCAGCCA
2601 CATCATGCTG GACGTGGCCA ACACCGACTT CCGCGTGCTG GAGCTGGTGC
2651 TGGAGGAGAC CAGCGTGATG CTGAACCTGG TGCCCATGGT GGCCACCGTG
2701 CGCATCTTCG CCGAGCTGGA GGGCGTGATC ATCTACACCC GCAACCACGA
2751 GGTGTGCGTG GAGACCATGT GCAACGAGTA CGTGCTGGCC GAGCTGGTGA
2801 AGCAGATCGC CGTGGGCGGC GCCGTGGCCA GCGTGACCGT GCGCAGCCAC
2851 TGCGTGAGCA AGATCATGCG CGAGTTCAAC AGCTACAAGG GCCCCATCAG
```

FIG. 12B

```
2901  CCACGGCCAC GTGCTGAAGG CCTACGCCCA GAAGATCTTC AAGATCCTGC
2951  AGTACGACCC CGTGGCCGCC CTGTTCTACG TGAAGGTGTA CCTGGAGAGC
3001  TTCGACATCT ACCGCATCTT CGCCGAGCTG GTGTTCGAGA CCAGCGGCGG
3051  CCTGGTGGTG AAGGCCCGCG ACCACCTGGC CGTGCTGAAG GCCCGCGCCA
3101  AGAAGGACGA GCTGACCCGC GCCACCAAGA TGCAGGTGAT CCACGAGCTG
3151  CTGGTGCTGG TGAAGAAGGC CCAGCTGGAC GACTACAGCA ACACCCACAG
3201  CACCCGCTAC GTGCAGATCA AGGTGCGCGT GGACATGGTG CGCCGCCGCC
3251  ACCGCCAGGA CGCCCTGGCC CGCGTGTACG AGATCAAGTG CCGCAACGTG
3301  CGCCGCAGCT GGGAGGAGCT GTGCCCAGC CAGGAGCCCA TGAGCATCTA
3351  CGTGTACCAG GCCCGCCTGA CCGTGAGCGG CCTGGAGCTG CGCCGCAAGA
3401  TGATGTACAT GATCCCCAGC ATCAACGTGC ACCACTACTT CGAGCAGCCC
3451  ACCGAGACCC CCCCTACGC CTACATCTAC ACCACCTACC TGCAGGAGTT
3501  CTTCTGGGAC GCCAACGACA TCTACTACGA GCAGCACAAG ATCACCAGCT
3551  ACCAGGAGCC CATGAGCATC TACGTGTACA GCGAGCACCC CACCTTCACC
3601  AGCCAGTACC AGGCCATCCG CGAGACCGTG GAGCTGAAGC TTATCGATTG
3651  CGAGGACGTG CCCAGCGGCA AGCTGAAGAT GCAGGTGATC GGCGACCAGT
3701  ACGCCACCGT GCAGGGCCAG AACCTGAAGC ACGAGCGCAA CGGCTTCACC
3751  GTGCTGGACG CCCTGCCCGG CCCTGCATC GTGTACGCCC TGCCCCTGAA
3801  GATGCTGCCC ACCTTCACCA GCCAGTACCG CATCCAGGGC AAGCTGCAGA
3851  TGTGGCAGGC CCGCCTGACC GTGcatcatc atcatcatca ttgaCTCGAG
```
(SEQ ID NO: 4)

*FIG. 12B cont'd*

SEQUENCE LISTING

<160> NUMBER OF SEQ ID NOS: 87

<210> SEQ ID NO 1
<211> LENGTH: 1136
<212> TYPE: PRT
<213> ORGANISM: Human cytomegalovirus

<400> SEQUENCE: 1

```
Met Glu Ser Arg Ile Trp Cys Leu Val Val Cys Val Asn Leu Cys Ile
1               5                   10                  15

Val Cys Leu Gly Ala Ala Val Ser Ser Ser Ser Thr Ser His Ala Thr
            20                  25                  30

Ser Ser Thr His Asn Gly Ser His Thr Ser Arg Thr Thr Ser Ala Gln
        35                  40                  45

Thr Arg Ser Val Tyr Ser Gln His Val Thr Ser Ser Glu Ala Val Ser
    50                  55                  60

His Arg Ala Asn Glu Thr Ile Tyr Asn Thr Thr Leu Lys Tyr Gly Asp
65                  70                  75                  80

Val Val Gly Val Asn Thr Thr Lys Tyr Pro Tyr Arg Val Cys Ser Met
                85                  90                  95

Ala Gln Gly Thr Asp Leu Ile Arg Phe Glu Arg Asn Ile Ile Cys Thr
            100                 105                 110

Ser Met Lys Pro Ile Asn Glu Asp Leu Asp Glu Gly Ile Met Val Val
        115                 120                 125
```

```
Tyr Lys Arg Asn Ile Val Ala His Thr Phe Lys Val Arg Val Tyr Gln
    130                 135                 140

Lys Val Leu Thr Phe Arg Arg Ser Tyr Ala Tyr Ile Tyr Thr Thr Tyr
145                 150                 155                 160

Leu Leu Gly Ser Asn Thr Glu Tyr Val Ala Pro Pro Met Trp Glu Ile
                165                 170                 175

His His Ile Asn Lys Phe Ala Gln Cys Tyr Ser Ser Tyr Ser Arg Val
            180                 185                 190

Ile Gly Gly Thr Val Phe Val Ala Tyr His Arg Asp Ser Tyr Glu Asn
        195                 200                 205

Lys Thr Met Gln Leu Ile Pro Asp Asp Tyr Ser Asn Thr His Ser Thr
210                 215                 220

Arg Tyr Val Thr Val Lys Asp Gln Trp His Ser Arg Gly Ser Thr Trp
225                 230                 235                 240

Leu Tyr Arg Glu Thr Cys Asn Leu Asn Cys Met Leu Thr Ile Thr Thr
                245                 250                 255

Ala Arg Ser Lys Tyr Pro Tyr His Phe Phe Ala Thr Ser Thr Gly Asp
            260                 265                 270

Val Val Tyr Ile Ser Pro Phe Tyr Asn Gly Thr Asn Arg Asn Ala Ser
        275                 280                 285

Tyr Phe Gly Glu Asn Ala Asp Lys Phe Phe Ile Phe Pro Asn Tyr Thr
290                 295                 300

Ile Val Ser Asp Phe Gly Arg Pro Asn Ala Ala Pro Glu Thr His Arg
305                 310                 315                 320

Leu Val Ala Phe Leu Glu Arg Ala Asp Ser Val Ile Ser Trp Asp Ile
                325                 330                 335

Gln Asp Glu Lys Asn Val Thr Cys Gln Leu Thr Phe Trp Glu Ala Ser
            340                 345                 350

Glu Arg Thr Ile Arg Ser Glu Ala Glu Asp Ser Tyr His Phe Ser Ser
        355                 360                 365

Ala Lys Met Thr Ala Thr Phe Leu Ser Lys Lys Gln Glu Val Asn Met
370                 375                 380

Ser Asp Ser Ala Leu Asp Cys Val Arg Asp Glu Ala Ile Asn Lys Leu
385                 390                 395                 400

Gln Gln Ile Phe Asn Thr Ser Tyr Asn Gln Thr Tyr Glu Lys Tyr Gly
                405                 410                 415

Asn Val Ser Val Phe Glu Thr Ser Gly Gly Leu Val Val Phe Trp Gln
            420                 425                 430

Gly Ile Lys Gln Lys Ser Leu Val Glu Leu Glu Arg Leu Ala Asn Arg
        435                 440                 445

Ser Ser Leu Asn Ile Thr His Arg Thr Arg Ser Thr Ser Asp Asn
450                 455                 460

Asn Thr Thr His Leu Ser Ser Met Glu Ser Val His Asn Leu Val Tyr
465                 470                 475                 480

Ala Gln Leu Gln Phe Thr Tyr Asp Thr Leu Arg Gly Tyr Ile Asn Arg
                485                 490                 495

Ala Leu Ala Gln Ile Ala Glu Ala Trp Cys Val Asp Gln Arg Arg Thr
            500                 505                 510

Leu Glu Val Phe Lys Glu Leu Ser Lys Ile Asn Pro Ser Ala Ile Leu
        515                 520                 525

Ser Ala Ile Tyr Asn Lys Pro Ile Ala Ala Arg Phe Met Gly Asp Val
530                 535                 540

Leu Gly Leu Ala Ser Cys Val Thr Ile Asn Gln Thr Ser Val Lys Val
```

```
                545                 550                 555                 560
Leu Arg Asp Met Asn Val Lys Glu Ser Pro Gly Arg Cys Tyr Ser Arg
                565                 570                 575

Pro Val Val Ile Phe Asn Phe Ala Asn Ser Ser Tyr Val Gln Tyr Gly
                580                 585                 590

Gln Leu Gly Glu Asp Asn Glu Ile Leu Leu Gly Asn His Arg Thr Glu
                595                 600                 605

Glu Cys Gln Leu Pro Ser Leu Lys Ile Phe Ile Ala Gly Asn Ser Ala
                610                 615                 620

Tyr Glu Tyr Val Asp Tyr Leu Phe Lys Arg Met Ile Asp Leu Ser Ser
625                 630                 635                 640

Ile Ser Thr Val Asp Ser Met Ile Ala Leu Asp Ile Asp Pro Leu Glu
                645                 650                 655

Asn Thr Asp Phe Arg Val Leu Glu Leu Tyr Ser Gln Lys Glu Leu Arg
                660                 665                 670

Ser Ser Asn Val Phe Asp Leu Glu Glu Ile Met Arg Glu Phe Asn Ser
                675                 680                 685

Tyr Lys Gln Arg Val Lys Tyr Val Glu Asp Lys Val Val Thr Glu His
                690                 695                 700

Asp Thr Leu Leu Tyr Lys Pro Gly Lys Ile Ser His Ile Met Leu Asp
705                 710                 715                 720

Val Ala Asn Thr Asp Phe Arg Val Leu Glu Leu Val Leu Glu Glu Thr
                725                 730                 735

Ser Val Met Leu Asn Leu Val Pro Met Val Ala Thr Val Arg Ile Phe
                740                 745                 750

Ala Glu Leu Glu Gly Val Ile Ile Tyr Thr Arg Asn His Glu Val Cys
                755                 760                 765

Val Glu Thr Met Cys Asn Glu Tyr Val Leu Ala Glu Leu Val Lys Gln
                770                 775                 780

Ile Ala Val Gly Gly Ala Val Ala Ser Val Thr Val Arg Ser His Cys
785                 790                 795                 800

Val Ser Lys Ile Met Arg Glu Phe Asn Ser Tyr Lys Gly Pro Ile Ser
                805                 810                 815

His Gly His Val Leu Lys Ala Tyr Ala Gln Lys Ile Phe Lys Ile Leu
                820                 825                 830

Gln Tyr Asp Pro Val Ala Ala Leu Phe Tyr Val Lys Val Tyr Leu Glu
                835                 840                 845

Ser Phe Asp Ile Tyr Arg Ile Phe Ala Glu Leu Val Phe Glu Thr Ser
                850                 855                 860

Gly Gly Leu Val Val Lys Ala Arg Asp His Leu Ala Val Leu Lys Ala
865                 870                 875                 880

Arg Ala Lys Lys Asp Glu Leu Thr Arg Ala Thr Lys Met Gln Val Ile
                885                 890                 895

His Glu Leu Leu Val Leu Val Lys Lys Ala Gln Leu Asp Asp Tyr Ser
                900                 905                 910

Asn Thr His Ser Thr Arg Tyr Val Gln Ile Lys Val Arg Val Asp Met
                915                 920                 925

Val Arg Arg Arg His Arg Gln Asp Ala Leu Ala Arg Val Tyr Glu Ile
                930                 935                 940

Lys Cys Arg Asn Val Arg Arg Ser Trp Glu Glu Leu Cys Pro Ser Gln
945                 950                 955                 960

Glu Pro Met Ser Ile Tyr Val Tyr Gln Ala Arg Leu Thr Val Ser Gly
                965                 970                 975
```

-continued

```
Leu Glu Leu Arg Arg Lys Met Met Tyr Met Ile Pro Ser Ile Asn Val
            980                 985                 990

His His Tyr Phe Glu Gln Pro Thr Glu Thr Pro Pro Tyr Ala Tyr Ile
            995                 1000                1005

Tyr Thr Thr Tyr Leu Gln Glu Phe Phe Trp Asp Ala Asn Asp Ile
        1010                1015                1020

Tyr Tyr Glu Gln His Lys Ile Thr Ser Tyr Gln Glu Pro Met Ser
        1025                1030                1035

Ile Tyr Val Tyr Ser Glu His Pro Thr Phe Thr Ser Gln Tyr Gln
        1040                1045                1050

Ala Ile Arg Glu Thr Val Glu Leu Cys Glu Asp Val Pro Ser Gly
        1055                1060                1065

Lys Leu Lys Met Gln Val Ile Gly Asp Gln Tyr Ala Thr Val Gln
        1070                1075                1080

Gly Gln Asn Leu Lys His Glu Arg Asn Gly Phe Thr Val Leu Asp
        1085                1090                1095

Ala Leu Pro Gly Pro Cys Ile Val Tyr Ala Leu Pro Leu Lys Met
        1100                1105                1110

Leu Pro Thr Phe Thr Ser Gln Tyr Arg Ile Gln Gly Lys Leu Gln
        1115                1120                1125

Met Trp Gln Ala Arg Leu Thr Val
        1130                1135

<210> SEQ ID NO 2
<211> LENGTH: 1299
<212> TYPE: PRT
<213> ORGANISM: Human cytomegalovirus

<400> SEQUENCE: 2

Gly Thr Ala Ala Thr Met Asp Ala Met Lys Arg Gly Leu Cys Cys Val
1               5                   10                  15

Leu Leu Leu Cys Gly Ala Val Phe Val Ser Pro Ser Gln Glu Ile His
            20                  25                  30

Ala Arg Phe Arg Arg Gly Ala Arg Ala Ser Ser Ser Thr Ser His Ala
        35                  40                  45

Thr Ser Ser Thr His Asn Gly Ser His Thr Ser Arg Thr Thr Ser Ala
    50                  55                  60

Gln Thr Arg Ser Val Tyr Ser Gln His Val Thr Ser Ser Glu Ala Val
65                  70                  75                  80

Ser His Arg Ala Asn Glu Thr Ile Tyr Asn Thr Thr Leu Lys Tyr Gly
                85                  90                  95

Asp Val Val Gly Val Asn Thr Thr Lys Tyr Pro Tyr Arg Val Cys Ser
            100                 105                 110

Met Ala Gln Gly Thr Asp Leu Ile Arg Phe Glu Arg Asn Ile Ile Cys
        115                 120                 125

Thr Ser Met Lys Pro Ile Asn Glu Asp Leu Asp Glu Gly Ile Met Val
    130                 135                 140

Val Tyr Lys Arg Asn Ile Val Ala His Thr Phe Lys Val Arg Val Tyr
145                 150                 155                 160

Gln Lys Val Leu Thr Phe Arg Arg Ser Tyr Ala Tyr Ile Tyr Thr Thr
                165                 170                 175

Tyr Leu Leu Gly Ser Asn Thr Glu Tyr Val Ala Pro Pro Met Trp Glu
            180                 185                 190

Ile His His Ile Asn Lys Phe Ala Gln Cys Tyr Ser Ser Tyr Ser Arg
        195                 200                 205
```

-continued

| | | | | | | | | | | | | |
|---|---|---|---|---|---|---|---|---|---|---|---|---|
| Val | Ile | Gly | Gly | Thr | Val | Phe | Val | Ala | Tyr | His | Arg | Asp | Ser | Tyr | Glu |
| | 210 | | | | 215 | | | | 220 | | | |

Asn Lys Thr Met Gln Leu Ile Pro Asp Asp Tyr Ser Asn Thr His Ser
225 230 235 240

Thr Arg Tyr Val Thr Val Lys Asp Gln Trp His Ser Arg Gly Ser Thr
245 250 255

Trp Leu Tyr Arg Glu Thr Cys Asn Leu Asn Cys Met Leu Thr Ile Thr
260 265 270

Thr Ala Arg Ser Lys Tyr Pro Tyr His Phe Phe Ala Thr Ser Thr Gly
275 280 285

Asp Val Val Tyr Ile Ser Pro Phe Tyr Asn Gly Thr Asn Arg Asn Ala
290 295 300

Ser Tyr Phe Gly Glu Asn Ala Asp Lys Phe Phe Ile Phe Pro Asn Tyr
305 310 315 320

Thr Ile Val Ser Asp Phe Gly Arg Pro Asn Ala Ala Pro Glu Thr His
325 330 335

Arg Leu Val Ala Phe Leu Glu Arg Ala Asp Ser Val Ile Ser Trp Asp
340 345 350

Ile Gln Asp Glu Lys Asn Val Thr Cys Gln Leu Thr Phe Trp Glu Ala
355 360 365

Ser Glu Arg Thr Ile Arg Ser Glu Ala Glu Asp Ser Tyr His Phe Ser
370 375 380

Ser Ala Lys Met Thr Ala Thr Phe Leu Ser Lys Lys Gln Glu Val Asn
385 390 395 400

Met Ser Asp Ser Ala Leu Asp Cys Val Arg Asp Glu Ala Ile Asn Lys
405 410 415

Leu Gln Gln Ile Phe Asn Thr Ser Tyr Asn Gln Thr Tyr Glu Lys Tyr
420 425 430

Gly Asn Val Ser Val Phe Glu Thr Ser Gly Gly Leu Val Val Phe Trp
435 440 445

Gln Gly Ile Lys Gln Lys Ser Leu Val Glu Leu Glu Arg Leu Ala Asn
450 455 460

Arg Ser Ser Leu Asn Ile Thr His Arg Thr Arg Arg Ser Thr Ser Asp
465 470 475 480

Asn Asn Thr Thr His Leu Ser Ser Met Glu Ser Val His Asn Leu Val
485 490 495

Tyr Ala Gln Leu Gln Phe Thr Tyr Asp Thr Leu Arg Gly Tyr Ile Asn
500 505 510

Arg Ala Leu Ala Gln Leu Ala Glu Ala Trp Cys Val Asp Gln Arg Arg
515 520 525

Thr Leu Glu Val Phe Lys Glu Leu Ser Lys Ile Asn Pro Ser Ala Ile
530 535 540

Leu Ser Ala Ile Tyr Asn Lys Pro Leu Ala Ala Arg Phe Met Gly Asp
545 550 555 560

Val Leu Gly Leu Ala Ser Cys Val Thr Ile Asn Gln Thr Ser Val Lys
565 570 575

Val Leu Arg Asp Met Asn Val Lys Glu Ser Pro Gly Arg Cys Tyr Ser
580 585 590

Arg Pro Val Val Ile Phe Asn Phe Ala Asn Ser Ser Tyr Val Gln Tyr
595 600 605

Gly Gln Leu Gly Glu Asp Asn Glu Ile Leu Leu Gly Asn His Arg Thr
610 615 620

Glu Glu Cys Gln Leu Pro Ser Leu Lys Ile Phe Ile Ala Gly Asn Ser
625 630 635 640

-continued

```
Ala Tyr Glu Tyr Val Asp Tyr Leu Phe Lys Arg Met Ile Asp Leu Ser
                645                 650                 655

Ser Ile Ser Thr Val Asp Ser Met Ile Ala Leu Asp Ile Asp Pro Leu
                660                 665                 670

Glu Asn Thr Asp Phe Arg Val Leu Glu Leu Tyr Ser Gln Lys Glu Leu
                675                 680                 685

Arg Ser Ser Asn Val Phe Asp Leu Glu Glu Ile Met Arg Glu Phe Asn
                690                 695                 700

Ser Tyr Lys Gln Arg Val Lys Tyr Val Glu Asp Lys Val Lys Leu Cys
705                 710                 715                 720

Thr Gln Pro Leu Gln Asn Leu Phe Pro Tyr Leu Val Ser Ala Asp Gly
                725                 730                 735

Thr Thr Val Thr Ser Gly Ser Thr Lys Asp Thr Ser Leu Gln Ala Pro
                740                 745                 750

Pro Ser Tyr Glu Glu Ser Val Tyr Asn Ser Gly Arg Lys Gly Pro Gly
                755                 760                 765

Pro Pro Ser Ser Asp Ala Ser Thr Ala Ala Pro Pro Tyr Thr Asn Glu
                770                 775                 780

Gln Ala Tyr Gln Met Leu Leu Ala Leu Ala Arg Leu Asp Ala Glu Gln
785                 790                 795                 800

Arg Ala Gln Gln Asn Gly Thr Asp Ser Leu Asp Gly Gln Thr Gly Thr
                805                 810                 815

Gln Asp Lys Gly Gln Lys Pro Asn Leu Leu Asp Arg Leu Arg His Arg
                820                 825                 830

Lys Asn Gly Tyr Arg His Leu Lys Asp Ser Asp Glu Glu Asn Val
                835                 840                 845

Ala Ala Ala Val Thr Glu His Asp Thr Leu Leu Tyr Lys Pro Gly Lys
                850                 855                 860

Ile Ser His Ile Met Leu Asp Val Ala Asn Thr Asp Phe Arg Val Leu
865                 870                 875                 880

Glu Leu Val Leu Glu Glu Thr Ser Val Met Leu Asn Leu Val Pro Met
                885                 890                 895

Val Ala Thr Val Arg Ile Phe Ala Glu Leu Glu Gly Val Ile Ile Tyr
                900                 905                 910

Thr Arg Asn His Glu Val Cys Val Glu Thr Met Cys Asn Glu Tyr Val
                915                 920                 925

Leu Ala Glu Leu Val Lys Gln Ile Ala Val Gly Gly Ala Val Ala Ser
930                 935                 940

Val Thr Val Arg Ser His Cys Val Ser Lys Ile Met Arg Glu Phe Asn
945                 950                 955                 960

Ser Tyr Lys Gly Pro Ile Ser His Gly His Val Leu Lys Ala Tyr Ala
                965                 970                 975

Gln Lys Ile Phe Lys Ile Leu Gln Tyr Asp Pro Val Ala Ala Leu Phe
                980                 985                 990

Tyr Val Lys Val Tyr Leu Glu Ser Phe Asp Ile Tyr Arg Ile Phe Ala
                995                1000                1005

Glu Leu Val Phe Glu Thr Ser Gly Gly Leu Val Val Lys Ala Arg
                1010                1015                1020

Asp His Leu Ala Val Leu Lys Ala Arg Ala Lys Lys Asp Glu Leu
                1025                1030                1035

Thr Arg Ala Thr Lys Met Gln Val Ile His Glu Leu Leu Val Leu
                1040                1045                1050

Val Lys Lys Ala Gln Leu Asp Asp Tyr Ser Asn Thr His Ser Thr
```

-continued

```
                1055                1060                1065

Arg Tyr Val Gln Ile Lys Val Arg Val Asp Met Val Arg Arg Arg
    1070                1075                1080

His Arg Gln Asp Ala Leu Ala Arg Val Tyr Glu Ile Lys Cys Arg
    1085                1090                1095

Asn Val Arg Arg Ser Trp Glu Glu Leu Cys Pro Ser Gln Glu Pro
    1100                1105                1110

Met Ser Ile Tyr Val Tyr Gln Ala Arg Leu Thr Val Ser Gly Leu
    1115                1120                1125

Glu Leu Arg Arg Lys Met Met Tyr Met Ile Pro Ser Ile Asn Val
    1130                1135                1140

His His Tyr Phe Glu Gln Pro Thr Glu Thr Pro Pro Tyr Ala Tyr
    1145                1150                1155

Ile Tyr Thr Thr Tyr Leu Gln Glu Phe Phe Trp Asp Ala Asn Asp
    1160                1165                1170

Ile Tyr Tyr Glu Gln His Lys Ile Thr Ser Tyr Gln Glu Pro Met
    1175                1180                1185

Ser Ile Tyr Val Tyr Ser Glu His Pro Thr Phe Thr Ser Gln Tyr
    1190                1195                1200

Gln Ala Ile Arg Glu Thr Val Glu Leu Lys Leu Ile Asp Cys Glu
    1205                1210                1215

Asp Val Pro Ser Gly Lys Leu Lys Met Gln Val Ile Gly Asp Gln
    1220                1225                1230

Tyr Ala Thr Val Gln Gly Gln Asn Leu Lys His Glu Arg Asn Gly
    1235                1240                1245

Phe Thr Val Leu Asp Ala Leu Pro Gly Pro Cys Ile Val Tyr Ala
    1250                1255                1260

Leu Pro Leu Lys Met Leu Pro Thr Phe Thr Ser Gln Tyr Arg Ile
    1265                1270                1275

Gln Gly Lys Leu Gln Met Trp Gln Ala Arg Leu Thr Val His His
    1280                1285                1290

His His His His Leu Glu
    1295

<210> SEQ ID NO 3
<211> LENGTH: 3426
<212> TYPE: DNA
<213> ORGANISM: Human cytomegalovirus

<400> SEQUENCE: 3
atggaatcca ggatctggtg cctggtagtc tgcgttaacc tgtgtatcgt ctgtctgggt      60
gctgcggttt cctcttctag tacttcccat gcaacttctt ctactcacaa tggaagccat     120
acttctcgta cgacgtctgc tcaaacccgg tcagtctatt ctcaacacgt aacgtcttct     180
gaagccgtca gtcatagagc caacgagact atctacaaca ctaccctcaa gtacggagat     240
gtggtgggag tcaacactac caagtacccc atcgcgtgt gttctatggc ccagggtacg      300
gatcttattc gctttgaacg taatatcatc tgcacctcga tgaagcctat caatgaagac     360
ttggatgagg gcatcatggt ggtctacaag cgcaacatcg tggcgcacac ctttaaggta     420
cgggtctacc aaaaggtttt gacgtttcgt cgtagctacg cttacatcta caccactttat    480 ctgctgggca gcaatacgga atacgtggcg cctcctatgt gggagattca tcacatcaac     540
aagtttgctc aatgctacag ttcctacagc cgcgttatag aggcacggtt ttcgtggca    600 tatcataggg acagttatga aacaaaaacc atgcaattaa ttcccgacga ttattccaac     660
```

```
acccacagta cccgttacgt gacggtcaag gatcagtggc acagccgcgg cagcacctgg      720
ctctatcgtg agacctgtaa tctgaactgt atgctgacca tcactactgc gcgctccaag      780
tatccttatc attttttgc aacttccacg ggtgatgtgg tttacatttc tcctttctac      840
aacggaacca atcgcaatgc cagctacttt ggagaaaacg ccgacaagtt tttcattttc      900
ccgaactaca ccatcgtttc cgactttgga agacccaacg ctgcgccaga acccatagg      960 ttggtggctt ttctcgaacg tgccgactcg gtgatctctt gggatataca ggacgagaag    1020
aatgtcacct gccagctcac cttctgggaa gcctcggaac gtactatccg ttccgaagcc    1080
gaagactcgt accactttc ttctgccaaa atgactgcaa cttttctgtc taagaaacaa    1140
gaagtgaaca tgtccgactc cgcgctggac tgcgtacgtg atgaggctat aaataagtta    1200
cagcagattt tcaatacttc atacaatcaa acatatgaaa aatacggaaa cgtgtccgtc    1260
ttcgaaacca gcggcggtct ggtggtgttc tggcaaggca tcaagcaaaa atctttggtg    1320
gaattggaac gtttggccaa tcgatccagt ctgaatatca ctcataggac cagaagaagt    1380
acgagtgaca ataatacaac tcatttgtcc agcatggaat cggtgcacaa tctggtctac    1440
gcccagctgc agttcaccta tgacacgttg cgcggttaca tcaaccgggc gctggcgcaa    1500
atcgcagaag cctggtgtgt ggatcaacgg cgcaccctag aggtcttcaa ggaactcagc    1560
aagatcaacc cgtcagccat tctctcggcc atttacaaca aaccgattgc cgcgcgtttc    1620
atgggtgatg tcttgggcct ggccagctgc gtgaccatca accaaaccag cgtcaaggtg    1680
ctgcgtgata tgaacgtgaa ggaatcgcca ggacgctgct actcacgacc cgtggtcatc    1740
tttaatttcg ccaacagctc gtacgtgcag tacggtcaac tgggcgagga caacgaaatc    1800
ctgttgggca accaccgcac tgaggaatgt cagcttccca gcctcaagat cttcatcgcc    1860
gggaactcgg cctacgagta cgtggactac ctcttcaaac gcatgattga cctcagcagt    1920
atctccaccg tcgacagcat gatcgccctg gatatcgacc cgctggaaaa taccgacttc    1980
agggtactgg aactttactc gcagaaagag ctgcgttcca gcaacgtttt tgacctcgaa    2040
gagatcatgc gcgaattcaa ctcgtacaag cagcgggtaa agtacgtgga ggacaaggta    2100
aagcttgtga ccgagcacga caccctgctg tacaagcccg gcaagatcag ccacatcatg    2160
ctggacgtgg ccaacaccga cttccgcgtg ctggagctgg tgctggagga ccagcgtgtg    2220
atgctgaacc tggtgcccat ggtggccacc gtgcgcatct cgccgagct ggagggcgtg    2280 atcatctaca cccgcaacca cgaggtgtgc gtggagacca tgtgcaacga gtacgtgctg    2340
gccgagctgc tgaagcagat cgccgtgggc ggcgccgtgg ccagcgtgac cgtgcgcagc    2400
cactgcgtga gcaagatcat gcgcgagttc aacagctaca agggccccat cagccacggc    2460
cacgtgctga aggcctacgc ccagaagatc ttcaagatcc tgcagtacga ccccgtggcc    2520
gccctgttct acgtgaaggt gtacctggag agcttcgaca tctaccgcat cttcgccgag    2580
ctggtgttcg agaccagcgg cggcctggtg gtgaaggccc gcgaccacct ggccgtgctg    2640
aaggcccgcg ccaagaagga cgagctgacc cgcgccacca agatgcaggt gatccacgag    2700
ctgctggtgc tggtgaagaa ggcccagctg gacgactaca gcaacaccca cagcacccgc    2760
tacgtgcaga tcaaggtgcg cgtggacatg gtgcgccgcc gccaccgcca ggacgccctg    2820
gcccgcgtgt acgagatcaa gtgccgcaac gtgcgccgca gctgggagga gctgtgcccc    2880
agccaggagc ccatgagcat ctacgtgtac caggcccgcc tgaccgtgag cggcctggag    2940
ctgccgcgca agatgatgta catgatcccc agcatcaacg tgcaccacta cttcgagcag    3000
cccaccgaga cccccccccta cgcctacatc tacaccaccct acctgcagga gttcttctgg    3060
```

-continued

| | |
|---|---|
| gacgccaacg acatctacta cgagcagcac aagatcacca gctaccagga gcccatgagc | 3120 |
| atctacgtgt acagcgagca ccccaccttc accagccagt accaggccat ccgcgagacc | 3180 |
| gtggagctga agcttatcga ttgcgaggac gtgcccagcg gcaagctgaa gatgcaggtg | 3240 |
| atcggcgacc agtacgccac cgtgcagggc cagaacctga agcacgagcg caacggcttc | 3300 |
| accgtgctgg acgccctgcc cggcccctgc atcgtgtacg ccctgcccct gaagatgctg | 3360 |
| cccaccttca ccagccagta ccgcatccag ggcaagctgc agatgtggca ggcccgcctg | 3420 |
| accgtg | 3426 |

<210> SEQ ID NO 4
<211> LENGTH: 3900
<212> TYPE: DNA
<213> ORGANISM: Human cytomegalovirus

<400> SEQUENCE: 4

| | |
|---|---|
| ggtaccgccg ccaccatgga tgcaatgaag agagggctct gctgtgtgct gctgctgtgt | 60 |
| ggagcagtct tcgtttcgcc cagccaggaa atccatgccc gattcagaag aggcgccaga | 120 |
| gctagctcta gtacttccca tgcaacttct tctactcaca atggaagcca tacttctcgt | 180 |
| acgacgtctg ctcaaacccg gtcagtctat tctcaacacg taacgtcttc tgaagccgtc | 240 |
| agtcatagag ccaacgagac tatctacaac actaccctca agtacggaga tgtggtggga | 300 |
| gtcaacacta ccaagtaccc ctatcgcgtg tgttctatgg cccagggtac ggatcttatt | 360 |
| cgctttgaac gtaatatcat ctgcacctcg atgaagccta tcaatgaaga cttggatgag | 420 |
| ggcatcatgg tggtctacaa gcgcaacatc gtggcgcaca cctttaaggt acgggtctac | 480 |
| caaaaggttt tgacgtttcg tcgtagctac gcttacatct acaccactta tctgctgggc | 540 |
| agcaatacgg aatacgtggc gcctcctatg tgggagattc atcacatcaa caagtttgct | 600 |
| caatgctaca gttcctacag ccgcgttata ggaggcacgg ttttcgtggc atatcatagg | 660 |
| gacagttatg aaaacaaaac catgcaatta attcccgacg attattccaa cacccacagt | 720 |
| acccgttacg tgacggtcaa ggatcagtgg cacagccgcg gcagcacctg gctctatcgt | 780 |
| gagacctgta atctgaactg tatgctgacc atcactactg cgcgctccaa gtatccttat | 840 |
| catttttttg caacttccac gggtgatgtg gtttacattt ctcctttcta aacggaacc | 900 |
| aatcgcaatg ccagctactt tggagaaaac gccgacaagt ttttcatttt cccgaactac | 960 |
| accatcgttt ccgactttgg aagacccaac gctgcgccag aaacccatag gttggtggct | 1020 |
| tttctcgaac gtgccgactc ggtgatctct tgggatatac aggacgagaa gaatgtcacc | 1080 |
| tgccagctca ccttctggga agcctcggaa cgtactatcc gttccgaagc cgaagactcg | 1140 |
| taccacttttt cttctgccaa aatgactgca acttttctgt ctaagaaaca agaagtgaac | 1200 |
| atgtccgact ccgcgctgga ctgcgtacgt gatgaggcta taaataagtt acagcagatt | 1260 |
| ttcaatactt catacaatca aacatatgaa aaatacggaa acgtgtccgt cttcgaaacc | 1320 |
| agcggcggtc tggtggtgtt ctggcaaggc atcaagcaaa atctttggt ggaattggaa | 1380 |
| cgtttggcca atcgatccag tctgaatatc actcatagga ccagaagaag tacgagtgac | 1440 |
| aataatacaa ctcatttgtc cagcatggaa tcggtgcaca atctggtcta cgcccagctg | 1500 |
| cagttcacct atgacacgtt gcgcggttac atcaacgggg cgctggcgca atcgcagaa | 1560 |
| gcctggtgtg tggatcaacg gcgcacccta gaggtcttca aggaactcag caagatcaac | 1620 |
| ccgtcagcca ttctctcggc catttacaac aaaccgattg ccgcgcgttt catgggtgat | 1680 |
| gtcttgggcc tggccagctg cgtgaccatc aaccaaacca gcgtcaaggt gctgcgtgat | 1740 |

-continued

```
atgaacgtga aggaatcgcc aggacgctgc tactcacgac ccgtggtcat cttttaatttc      1800
gccaacagct cgtacgtgca gtacggtcaa ctgggcgagg acaacgaaat cctgttgggc      1860
aaccaccgca ctgaggaatg tcagcttccc agcctcaaga tcttcatcgc cgggaactcg      1920
gcctacgagt acgtggacta cctcttcaaa cgcatgattg acctcagcag tatctccacc      1980
gtcgacagca tgatcgccct ggatatcgac ccgctggaaa ataccgactt cagggtactg      2040
gaactttact cgcagaaaga gctgcgttcc agcaacgttt ttgacctcga agagatcatg      2100
cgcgaattca actcgtacaa gcagcgggta agtacgtgg aggacaaggt aaagctttgc       2160
acgcagccgc tgcagaacct ctttccctat ctggtgtccg ccgacgggac caccgtgacg      2220
tcgggcagca ccaaagacac gtcgttacag gctccgcctt cctacgagga agtgtttat       2280
aattctggtc gcaaaggacc gggaccaccg tcgtctgatg catccacggc ggctccgcct      2340
tacaccaacg agcaggctta ccagatgctt ctggccctgg cccgtctgga cgcagagcag      2400
cgagcgcagc agaacggtac agattctttg gacggacaga ctggcacgca ggacaaggga      2460
cagaagccta acctgctaga ccggctgcga catcgcaaaa acggctacag acacttgaaa      2520
gactccgacg aagaagagaa cgtcgcggcc gcggtgaccg agcacgacac cctgctgtac      2580
aagcccggca agatcagcca catcatgctg gacgtggcca acaccgactt ccgcgtgctg      2640
gagctggtgc tggaggagac cagcgtgatg ctgaacctgg tgcccatggt ggccaccgtg      2700
cgcatcttcg ccgagctgga gggcgtgatc atctacaccc gcaaccacga ggtgtgcgtg      2760
gagaccatgt gcaacgagta cgtgctggcc gagctggtga agcagatcgc cgtgggcggc      2820
gccgtggcca gcgtgaccgt gcgcagccac tgcgtgagca agatcatgcg cgagttcaac      2880
agctacaagg cccccatcag ccacggccac gtgctgaagg cctacgccca gaagatcttc      2940
aagatcctgc agtacgaccc cgtggccgcc ctgttctacg tgaaggtgta cctggagagc      3000
ttcgacatct accgcatctt cgccgagctg gtgttcgaga ccagcggcgg cctggtggtg      3060
aaggcccgcg accacctggc cgtgctgaag gcccgcgcca agaaggacga gctgacccgc      3120
gccaccaaga tgcaggtgat ccacgagctg ctggtgctgg tgaagaaggc ccagctggac      3180
gactacagca acacccacag caccgctac gtgcagatca aggtgcgcgt ggacatggtg       3240
cgccgccgcc accgccagga cgccctggcc cgcgtgtacg agatcaagtg ccgcaacgtg      3300
cgccgcagct gggaggagct gtgccccagc caggagccca tgagcatcta cgtgtaccag      3360
gcccgcctga ccgtgagcgg cctggagctg cgccgcaaga tgatgtacat gatccccagc      3420
atcaacgtgc accactactt cgagcagccc accgagaccc cccctacgc ctacatctac       3480
accacctacc tgcaggagtt cttctgggac gccaacgaca tctactacga gcagcacaag      3540
atcaccagct accaggagcc catgagcatc tacgtgtaca gcgagcaccc caccttcacc      3600
agccagtacc aggccatccg cgagaccgtg gagctgaagc ttatcgattg cgaggacgtg      3660
cccagcggca agctgaagat gcaggtgatc ggcgaccagt acgccaccgt gcagggccag      3720
aacctgaagc acgagcgcaa cggcttcacc gtgctggacg ccctgccgg ccctgcatc       3780
gtgtacgccc tgcccctgaa gatgctgccc accttcacca gccagtaccg catccagggc      3840
aagctgcaga tgtggcaggc ccgcctgacc gtgcatcatc atcatcatca ttgactcgag      3900
```

<210> SEQ ID NO 5
<211> LENGTH: 436
<212> TYPE: PRT
<213> ORGANISM: Human cytomegalovirus

<400> SEQUENCE: 5

-continued

```
Val Thr Glu His Asp Thr Leu Leu Tyr Asn Thr Asp Phe Arg Val Leu
1               5                   10                  15
Glu Leu Cys Val Glu Thr Met Cys Asn Glu Tyr Val Leu Glu Glu Thr
            20                  25                  30
Ser Val Met Leu Asn Leu Val Pro Met Val Ala Thr Val Arg Ile Phe
        35                  40                  45
Ala Glu Leu Glu Gly Val Ile Ile Tyr Thr Arg Asn His Glu Val Val
    50                  55                  60
Leu Ala Glu Leu Val Lys Gln Ile Ala Val Gly Gly Ala Val Ala Ser
65                  70                  75                  80
Val Thr Val Arg Ser His Cys Val Ser Lys Ile Met Arg Glu Phe Asn
                85                  90                  95
Ser Tyr Lys Gly Pro Ile Ser His Gly His Val Leu Lys Ala Thr Val
            100                 105                 110
Gln Gly Gln Asn Leu Lys Val Tyr Ala Leu Pro Leu Lys Met Leu Ala
        115                 120                 125
Tyr Ala Gln Lys Ile Phe Lys Ile Leu Gln Tyr Asp Pro Val Ala Ala
    130                 135                 140
Leu Phe Tyr Val Lys Val Tyr Leu Glu Ser Phe Asp Ile Tyr Arg Ile
145                 150                 155                 160
Phe Ala Glu Leu Val Phe Glu Thr Ser Gly Gly Leu Val Val Lys Ala
                165                 170                 175
Arg Asp His Leu Ala Val Leu Gln Ala Arg Leu Thr Val Ser Gly Leu
            180                 185                 190
Lys Ala Arg Ala Lys Lys Asp Glu Leu Gln Ile Lys Val Arg Val Asp
        195                 200                 205
Met Val Arg Arg His Arg Gln Asp Ala Leu Ala Arg Val Tyr Glu
    210                 215                 220
Ile Lys Cys Arg Lys Met Gln Val Ile Gly Asp Gln Tyr Asn Val Arg
225                 230                 235                 240
Arg Ser Trp Glu Glu Leu Cys Pro Ser Gln Glu Pro Met Ser Ile Tyr
                245                 250                 255
Val Tyr Lys Pro Gly Lys Ile Ser His Ile Met Leu Asp Val Ala Glu
            260                 265                 270
Leu Arg Arg Lys Met Met Tyr Met Ile Pro Ser Ile Asn Val His His
        275                 280                 285
Tyr Phe Glu Gln Pro Thr Glu Thr Pro Pro Tyr Ala Tyr Ile Tyr Thr
    290                 295                 300
Thr Tyr Leu Gln Glu Phe Phe Trp Asp Ala Asn Asp Ile Tyr Tyr Glu
305                 310                 315                 320
Gln His Lys Ile Thr Ser Tyr Gln Glu Pro Met Ser Ile Tyr Val Tyr
                325                 330                 335
Ser Glu His Pro Thr Phe Thr Ser Gln Tyr Gln Ala Ile Arg Glu Thr
            340                 345                 350
Val Glu Leu Thr Arg Ala Thr Lys Met Gln Val Ile Asp Ala Leu Pro
        355                 360                 365
Gly Pro Cys Ile Cys Glu Asp Val Pro Ser Gly Lys Leu Lys Met Gln
    370                 375                 380
Val Ile Gly Asp Gln Tyr Pro Thr Phe Thr Ser Gln Tyr Arg Ile Gln
385                 390                 395                 400
Gly Lys Leu Gln Met Trp Gln Ala Arg Leu Thr Val His Glu Leu Leu
                405                 410                 415
Val Leu Val Lys Lys Ala Gln Leu Asp Asp Tyr Ser Asn Thr His Ser
            420                 425                 430
```

```
Thr Arg Tyr Val
        435

<210> SEQ ID NO 6
<211> LENGTH: 9
<212> TYPE: PRT
<213> ORGANISM: Human cytomegalovirus

<400> SEQUENCE: 6

Val Thr Glu His Asp Thr Leu Leu Tyr
1               5

<210> SEQ ID NO 7
<211> LENGTH: 9
<212> TYPE: PRT
<213> ORGANISM: Human cytomegalovirus

<400> SEQUENCE: 7

Asn Thr Asp Phe Arg Val Leu Glu Leu
1               5

<210> SEQ ID NO 8
<211> LENGTH: 9
<212> TYPE: PRT
<213> ORGANISM: Human cytomegalovirus

<400> SEQUENCE: 8

Cys Val Glu Thr Met Cys Asn Glu Tyr
1               5

<210> SEQ ID NO 9
<211> LENGTH: 9
<212> TYPE: PRT
<213> ORGANISM: Human cytomegalovirus

<400> SEQUENCE: 9

Val Leu Glu Glu Thr Ser Val Met Leu
1               5

<210> SEQ ID NO 10
<211> LENGTH: 9
<212> TYPE: PRT
<213> ORGANISM: Human cytomegalovirus

<400> SEQUENCE: 10

Asn Leu Val Pro Met Val Ala Thr Val
1               5

<210> SEQ ID NO 11
<211> LENGTH: 9
<212> TYPE: PRT
<213> ORGANISM: Human cytomegalovirus

<400> SEQUENCE: 11

Arg Ile Phe Ala Glu Leu Glu Gly Val
1               5

<210> SEQ ID NO 12
<211> LENGTH: 9
<212> TYPE: PRT
<213> ORGANISM: Human cytomegalovirus

<400> SEQUENCE: 12

Ile Ile Tyr Thr Arg Asn His Glu Val
1               5
```

```
<210> SEQ ID NO 13
<211> LENGTH: 9
<212> TYPE: PRT
<213> ORGANISM: Human cytomegalovirus

<400> SEQUENCE: 13

Val Leu Ala Glu Leu Val Lys Gln Ile
1               5

<210> SEQ ID NO 14
<211> LENGTH: 9
<212> TYPE: PRT
<213> ORGANISM: Human cytomegalovirus

<400> SEQUENCE: 14

Ala Val Gly Gly Ala Val Ala Ser Val
1               5

<210> SEQ ID NO 15
<211> LENGTH: 9
<212> TYPE: PRT
<213> ORGANISM: Human cytomegalovirus

<400> SEQUENCE: 15

Thr Val Arg Ser His Cys Val Ser Lys
1               5

<210> SEQ ID NO 16
<211> LENGTH: 9
<212> TYPE: PRT
<213> ORGANISM: Human cytomegalovirus

<400> SEQUENCE: 16

Ile Met Arg Glu Phe Asn Ser Tyr Lys
1               5

<210> SEQ ID NO 17
<211> LENGTH: 10
<212> TYPE: PRT
<213> ORGANISM: Human cytomegalovirus

<400> SEQUENCE: 17

Gly Pro Ile Ser His Gly His Val Leu Lys
1               5                   10

<210> SEQ ID NO 18
<211> LENGTH: 9
<212> TYPE: PRT
<213> ORGANISM: Human cytomegalovirus

<400> SEQUENCE: 18

Ala Thr Val Gln Gly Gln Asn Leu Lys
1               5

<210> SEQ ID NO 19
<211> LENGTH: 9
<212> TYPE: PRT
<213> ORGANISM: Human cytomegalovirus

<400> SEQUENCE: 19

Val Tyr Ala Leu Pro Leu Lys Met Leu
1               5

<210> SEQ ID NO 20
```

```
<211> LENGTH: 10
<212> TYPE: PRT
<213> ORGANISM: Human cytomegalovirus

<400> SEQUENCE: 20

Ala Tyr Ala Gln Lys Ile Phe Lys Ile Leu
1               5                   10

<210> SEQ ID NO 21
<211> LENGTH: 9
<212> TYPE: PRT
<213> ORGANISM: Human cytomegalovirus

<400> SEQUENCE: 21

Gln Tyr Asp Pro Val Ala Ala Leu Phe
1               5

<210> SEQ ID NO 22
<211> LENGTH: 9
<212> TYPE: PRT
<213> ORGANISM: Human cytomegalovirus

<400> SEQUENCE: 22

Tyr Val Lys Val Tyr Leu Glu Ser Phe
1               5

<210> SEQ ID NO 23
<211> LENGTH: 9
<212> TYPE: PRT
<213> ORGANISM: Human cytomegalovirus

<400> SEQUENCE: 23

Asp Ile Tyr Arg Ile Phe Ala Glu Leu
1               5

<210> SEQ ID NO 24
<211> LENGTH: 9
<212> TYPE: PRT
<213> ORGANISM: Human cytomegalovirus

<400> SEQUENCE: 24

Val Phe Glu Thr Ser Gly Gly Leu Val
1               5

<210> SEQ ID NO 25
<211> LENGTH: 9
<212> TYPE: PRT
<213> ORGANISM: Human cytomegalovirus

<400> SEQUENCE: 25

Lys Ala Arg Asp His Leu Ala Val Leu
1               5

<210> SEQ ID NO 26
<211> LENGTH: 9
<212> TYPE: PRT
<213> ORGANISM: Human cytomegalovirus

<400> SEQUENCE: 26

Gln Ala Arg Leu Thr Val Ser Gly Leu
1               5

<210> SEQ ID NO 27
<211> LENGTH: 9
<212> TYPE: PRT
<213> ORGANISM: Human cytomegalovirus
```

<400> SEQUENCE: 27

Lys Ala Arg Ala Lys Lys Asp Glu Leu
1               5

<210> SEQ ID NO 28
<211> LENGTH: 9
<212> TYPE: PRT
<213> ORGANISM: Human cytomegalovirus

<400> SEQUENCE: 28

Gln Ile Lys Val Arg Val Asp Met Val
1               5

<210> SEQ ID NO 29
<211> LENGTH: 9
<212> TYPE: PRT
<213> ORGANISM: Human cytomegalovirus

<400> SEQUENCE: 29

Arg Arg Arg His Arg Gln Asp Ala Leu
1               5

<210> SEQ ID NO 30
<211> LENGTH: 9
<212> TYPE: PRT
<213> ORGANISM: Human cytomegalovirus

<400> SEQUENCE: 30

Ala Arg Val Tyr Glu Ile Lys Cys Arg
1               5

<210> SEQ ID NO 31
<211> LENGTH: 9
<212> TYPE: PRT
<213> ORGANISM: Human cytomegalovirus

<400> SEQUENCE: 31

Lys Met Gln Val Ile Gly Asp Gln Tyr
1               5

<210> SEQ ID NO 32
<211> LENGTH: 9
<212> TYPE: PRT
<213> ORGANISM: Human cytomegalovirus

<400> SEQUENCE: 32

Asn Val Arg Arg Ser Trp Glu Glu Leu
1               5

<210> SEQ ID NO 33
<211> LENGTH: 12
<212> TYPE: PRT
<213> ORGANISM: Human cytomegalovirus

<400> SEQUENCE: 33

Cys Pro Ser Gln Glu Pro Met Ser Ile Tyr Val Tyr
1               5                   10

<210> SEQ ID NO 34
<211> LENGTH: 13
<212> TYPE: PRT
<213> ORGANISM: Human cytomegalovirus

<400> SEQUENCE: 34

Lys Pro Gly Lys Ile Ser His Ile Met Leu Asp Val Ala
1               5                   10

<210> SEQ ID NO 35
<211> LENGTH: 9
<212> TYPE: PRT
<213> ORGANISM: Human cytomegalovirus

<400> SEQUENCE: 35

Glu Leu Arg Arg Lys Met Met Tyr Met
1               5

<210> SEQ ID NO 36
<211> LENGTH: 9
<212> TYPE: PRT
<213> ORGANISM: Human cytomegalovirus

<400> SEQUENCE: 36

Ile Pro Ser Ile Asn Val His His Tyr
1               5

<210> SEQ ID NO 37
<211> LENGTH: 9
<212> TYPE: PRT
<213> ORGANISM: Human cytomegalovirus

<400> SEQUENCE: 37

Phe Glu Gln Pro Thr Glu Thr Pro Pro
1               5

<210> SEQ ID NO 38
<211> LENGTH: 9
<212> TYPE: PRT
<213> ORGANISM: Human cytomegalovirus

<400> SEQUENCE: 38

Tyr Ala Tyr Ile Tyr Thr Thr Tyr Leu
1               5

<210> SEQ ID NO 39
<211> LENGTH: 11
<212> TYPE: PRT
<213> ORGANISM: Human cytomegalovirus

<400> SEQUENCE: 39

Gln Glu Phe Phe Trp Asp Ala Asn Asp Ile Tyr
1               5                   10

<210> SEQ ID NO 40
<211> LENGTH: 9
<212> TYPE: PRT
<213> ORGANISM: Human cytomegalovirus

<400> SEQUENCE: 40

Tyr Glu Gln His Lys Ile Thr Ser Tyr
1               5

<210> SEQ ID NO 41
<211> LENGTH: 9
<212> TYPE: PRT
<213> ORGANISM: Human cytomegalovirus

<400> SEQUENCE: 41

Gln Glu Pro Met Ser Ile Tyr Val Tyr
1               5

-continued

```
<210> SEQ ID NO 42
<211> LENGTH: 10
<212> TYPE: PRT
<213> ORGANISM: Human cytomegalovirus

<400> SEQUENCE: 42

Ser Glu His Pro Thr Phe Thr Ser Gln Tyr
1               5                   10

<210> SEQ ID NO 43
<211> LENGTH: 9
<212> TYPE: PRT
<213> ORGANISM: Human cytomegalovirus

<400> SEQUENCE: 43

Gln Ala Ile Arg Glu Thr Val Glu Leu
1               5

<210> SEQ ID NO 44
<211> LENGTH: 9
<212> TYPE: PRT
<213> ORGANISM: Human cytomegalovirus

<400> SEQUENCE: 44

Thr Arg Ala Thr Lys Met Gln Val Ile
1               5

<210> SEQ ID NO 45
<211> LENGTH: 8
<212> TYPE: PRT
<213> ORGANISM: Human cytomegalovirus

<400> SEQUENCE: 45

Asp Ala Leu Pro Gly Pro Cys Ile
1               5

<210> SEQ ID NO 46
<211> LENGTH: 9
<212> TYPE: PRT
<213> ORGANISM: Human cytomegalovirus

<400> SEQUENCE: 46

Cys Glu Asp Val Pro Ser Gly Lys Leu
1               5

<210> SEQ ID NO 47
<211> LENGTH: 9
<212> TYPE: PRT
<213> ORGANISM: Human cytomegalovirus

<400> SEQUENCE: 47

His Glu Arg Asn Gly Phe Thr Val Leu
1               5

<210> SEQ ID NO 48
<211> LENGTH: 13
<212> TYPE: PRT
<213> ORGANISM: Human cytomegalovirus

<400> SEQUENCE: 48

Pro Thr Phe Thr Ser Gln Tyr Arg Ile Gln Gly Lys Leu
1               5                   10

<210> SEQ ID NO 49
<211> LENGTH: 9
```

```
<212> TYPE: PRT
<213> ORGANISM: Human cytomegalovirus

<400> SEQUENCE: 49

Gln Met Trp Gln Ala Arg Leu Thr Val
1               5

<210> SEQ ID NO 50
<211> LENGTH: 12
<212> TYPE: PRT
<213> ORGANISM: Human cytomegalovirus

<400> SEQUENCE: 50

His Glu Leu Leu Val Leu Val Lys Lys Ala Gln Leu
1               5                   10

<210> SEQ ID NO 51
<211> LENGTH: 12
<212> TYPE: PRT
<213> ORGANISM: Human cytomegalovirus

<400> SEQUENCE: 51

Asp Asp Tyr Ser Asn Thr His Ser Thr Arg Tyr Val
1               5                   10

<210> SEQ ID NO 52
<211> LENGTH: 39
<212> TYPE: DNA
<213> ORGANISM: Human cytomegalovirus

<400> SEQUENCE: 52
cgcggatccg ccgccaccat ggaatccagg atctggtgc                         39

<210> SEQ ID NO 53
<211> LENGTH: 39
<212> TYPE: DNA
<213> ORGANISM: Human cytomegalovirus

<400> SEQUENCE: 53
cgcggatccg ccgccaccat ggcaacttct tctactcac                         39

<210> SEQ ID NO 54
<211> LENGTH: 34
<212> TYPE: DNA
<213> ORGANISM: Human cytomegalovirus

<400> SEQUENCE: 54
cccaagcttt accttgtcct ccacgtactt tacc                              34

<210> SEQ ID NO 55
<211> LENGTH: 92
<212> TYPE: DNA
<213> ORGANISM: Human cytomegalovirus

<400> SEQUENCE: 55
cccaagcttg ccgccaccat ggtgaccgag cacgacaccc tgctgtacaa gcccggcaag   60
atcagccaca tcatgctgga cgtggccaac ac                                92

<210> SEQ ID NO 56
<211> LENGTH: 80
<212> TYPE: DNA
<213> ORGANISM: Human cytomegalovirus

<400> SEQUENCE: 56
```

```
cccaagcttg tgaccgagca cgacaccctg ctgtacaagc ccggcaagat cagccacatc    60
atgctggacg tggccaacac                                                80

<210> SEQ ID NO 57
<211> LENGTH: 63
<212> TYPE: DNA
<213> ORGANISM: Human cytomegalovirus

<400> SEQUENCE: 57
acgctggtct cctccagcac cagctccagc acgcggaagt cggtgttggc cacgtccagc    60
atg                                                                  63

<210> SEQ ID NO 58
<211> LENGTH: 102
<212> TYPE: DNA
<213> ORGANISM: Human cytomegalovirus

<400> SEQUENCE: 58
gtggttcctg gtgtagatga tcacgccctc cagctcggcg aagatcctca cggtggccac    60
catgggcacc aggttcagca tcacgctggt ctcctccagc ac                      102

<210> SEQ ID NO 59
<211> LENGTH: 103
<212> TYPE: DNA
<213> ORGANISM: Human cytomegalovirus

<400> SEQUENCE: 59
ggccacggcg ccgcccacgg cgatctgctt caccagctcg gccagcacgt actcgttgca    60
catggtctcc acgcacacct cgtggttgcg ggtgtagatg atc                     103

<210> SEQ ID NO 60
<211> LENGTH: 102
<212> TYPE: DNA
<213> ORGANISM: Human cytomegalovirus

<400> SEQUENCE: 60
acgtggccgt ggctgatggg gcccttgtag ctgttgaact cgcgcatgat cttgctcacg    60
cagtggctgc gcacggtcac gctggccacg gcgccgccca cg                      102

<210> SEQ ID NO 61
<211> LENGTH: 100
<212> TYPE: DNA
<213> ORGANISM: Human cytomegalovirus

<400> SEQUENCE: 61
ggtacacctt cacgtagaac agggcggcca cggggtcgta ctgcaggatc ttgaagatct    60
tctgggcgta ggccttcagc acgtggccgt ggctgatggg                         100

<210> SEQ ID NO 62
<211> LENGTH: 102
<212> TYPE: DNA
<213> ORGANISM: Human cytomegalovirus

<400> SEQUENCE: 62
gtcgcgggcc ttcaccacca ggccgccgct ggtctcgaac accagctcgg cgaagatgcg    60
gtagatgtcg aagctctcca ggtacacctt cacgtagaac ag                      102

<210> SEQ ID NO 63
<211> LENGTH: 101
<212> TYPE: DNA
```

```
<213> ORGANISM: Human cytomegalovirus

<400> SEQUENCE: 63
agcagctcgt ggatcacctg catcttggtg gcgcgggtca gctcgtcctt cttggcgcgg      60
gccttcagca cggccaggtg gtcgcgggcc ttcaccacca g                         101

<210> SEQ ID NO 64
<211> LENGTH: 101
<212> TYPE: DNA
<213> ORGANISM: Human cytomegalovirus

<400> SEQUENCE: 64
tccacgcgca ccttgatctg cacgtagcgg gtgctgtggg tgttgctgta gtcgtccagc      60
tgggccttct tcaccagcac cagcagctcg tggatcacct g                         101

<210> SEQ ID NO 65
<211> LENGTH: 102
<212> TYPE: DNA
<213> ORGANISM: Human cytomegalovirus

<400> SEQUENCE: 65
ctcccagctc ctcctcacgt tcctgcactt gatctcgtac accctggcca gggcgtcctg      60
cctgtgcctc ctcctcacca tgtccaccct caccttgatc tg                        102

<210> SEQ ID NO 66
<211> LENGTH: 106
<212> TYPE: DNA
<213> ORGANISM: Human cytomegalovirus

<400> SEQUENCE: 66
catcttgcgg cgcagctcca ggccgctcac ggtcaggcgg gcctggtaca cgtagatgct      60
catgggctcc tggctggggc acagctcctc ccagctgcgg cgcacg                   106

<210> SEQ ID NO 67
<211> LENGTH: 102
<212> TYPE: DNA
<213> ORGANISM: Human cytomegalovirus

<400> SEQUENCE: 67
gtgtagatgt aggcgtaggg gggggtctcg gtgggctgct cgaagtagtg gtgcacgttg      60
atgctgggga tcatgtacat catcttcctc ttcagctcca gg                       102

<210> SEQ ID NO 68
<211> LENGTH: 100
<212> TYPE: DNA
<213> ORGANISM: Human cytomegalovirus

<400> SEQUENCE: 68
catgggctcc tggtagctgg tgatcttgtg ctgctcgtag tagatgtcgt tggcgtccca      60
gaagaactcc tgcaggtagg tggtgtatgt aggcgtaggg                          100

<210> SEQ ID NO 69
<211> LENGTH: 106
<212> TYPE: DNA
<213> ORGANISM: Human cytomegalovirus

<400> SEQUENCE: 69
ccgctcgaga agcttcagct ccacggtctc cctgatggcc tggtactggc tggtgaaggt      60
ggggtgctcg ctgtacacgt agatgccatg ggctcctggt agctgg                   106
```

```
<210> SEQ ID NO 70
<211> LENGTH: 22
<212> TYPE: DNA
<213> ORGANISM: Human cytomegalovirus

<400> SEQUENCE: 70
cccaagcttg ccgccaccat gg                                                  22

<210> SEQ ID NO 71
<211> LENGTH: 22
<212> TYPE: DNA
<213> ORGANISM: Human cytomegalovirus

<400> SEQUENCE: 71
cccaagcttg tgaccgagca cg                                                  22

<210> SEQ ID NO 72
<211> LENGTH: 22
<212> TYPE: DNA
<213> ORGANISM: Human cytomegalovirus

<400> SEQUENCE: 72
ccgctcgaga agcttcagct cc                                                  22

<210> SEQ ID NO 73
<211> LENGTH: 98
<212> TYPE: DNA
<213> ORGANISM: Human cytomegalovirus

<400> SEQUENCE: 73
ccatcgattg cgaggacgtg cccagcggca agctgaagat gcaggtgatc ggcgaccagt        60
acgccaccgt gcagggccag aacctgaagc acgagcgc                                98

<210> SEQ ID NO 74
<211> LENGTH: 91
<212> TYPE: DNA
<213> ORGANISM: Human cytomegalovirus

<400> SEQUENCE: 74
gcagcatctt caggggcagg gcgtacacga tgcaggggcc gggcagggcg tccagcacgg        60
tgaagccgtt gcgctcgtgc ttcaggttct g                                       91

<210> SEQ ID NO 75
<211> LENGTH: 94
<212> TYPE: DNA
<213> ORGANISM: Human cytomegalovirus

<400> SEQUENCE: 75
ccgctcgagc acggtcaggc gggcctgcca catctgcagc ttgccctgga tgcggtactg        60
gctggtgaag gtgggcagca tcttcagggg cagg                                    94

<210> SEQ ID NO 76
<211> LENGTH: 21
<212> TYPE: DNA
<213> ORGANISM: Human cytomegalovirus

<400> SEQUENCE: 76
ccatcgattg cgaggacgtg c                                                  21

<210> SEQ ID NO 77
<211> LENGTH: 20
<212> TYPE: DNA
```

<213> ORGANISM: Human cytomegalovirus

<400> SEQUENCE: 77
ccgctcgagc acggtcaggc                                          20

<210> SEQ ID NO 78
<211> LENGTH: 82
<212> TYPE: DNA
<213> ORGANISM: Human cytomegalovirus

<400> SEQUENCE: 78
cggggtaccg ccgccaccat ggatgcaatg aagagagggc tctgctgtgt gctgctgctg    60
tgtggagcag tcttcgtttc gc                                       82

<210> SEQ ID NO 79
<211> LENGTH: 81
<212> TYPE: DNA
<213> ORGANISM: Human cytomegalovirus

<400> SEQUENCE: 79
cccaagcttg ctagctagct ctggcgcctc ttctgaatcg ggcatggatt tcctggctgg    60
gcgaaacgaa gactgctcca c                                        81

<210> SEQ ID NO 80
<211> LENGTH: 37
<212> TYPE: DNA
<213> ORGANISM: Human cytomegalovirus

<400> SEQUENCE: 80
gaatatcact catcagacca cccagagtac gagtgac                        37

<210> SEQ ID NO 81
<211> LENGTH: 37
<212> TYPE: DNA
<213> ORGANISM: Human cytomegalovirus

<400> SEQUENCE: 81
gtcactcgta ctctgggtgg tctgatgagt gatattc                        37

<210> SEQ ID NO 82
<211> LENGTH: 34
<212> TYPE: DNA
<213> ORGANISM: Human cytomegalovirus

<400> SEQUENCE: 82
gctctagagc tagctctagt acttcccatg caac                          34

<210> SEQ ID NO 83
<211> LENGTH: 28
<212> TYPE: DNA
<213> ORGANISM: Human cytomegalovirus

<400> SEQUENCE: 83
ccggaattcc gcggctgtgc cactgatc                                 28

<210> SEQ ID NO 84
<211> LENGTH: 28
<212> TYPE: DNA
<213> ORGANISM: Human cytomegalovirus

<400> SEQUENCE: 84
cgacaagctt tgcacgcagc cgctgcag                                 28

```
<210> SEQ ID NO 85
<211> LENGTH: 30
<212> TYPE: DNA
<213> ORGANISM: Human cytomegalovirus

<400> SEQUENCE: 85
gagtgcggcc gcgacgttct cttcttcgtc                                    30

<210> SEQ ID NO 86
<211> LENGTH: 28
<212> TYPE: DNA
<213> ORGANISM: Human cytomegalovirus

<400> SEQUENCE: 86
cgacaagctt tgcacgcagc cgctgcag                                      28

<210> SEQ ID NO 87
<211> LENGTH: 49
<212> TYPE: DNA
<213> ORGANISM: Human cytomegalovirus

<400> SEQUENCE: 87
ccgctcgagt caatgatgat gatgatgatg cacggtcagg cgggcctgc                49
```

HUMAN CYTOMEGALOVIRUS IMMUNOTHERAPY

This application is U.S. National Phase of International Application No. PCT/AU2005/001798, filed Nov. 29, 2005 designating the U.S., and published in English as WO 2006/056027 A1 on Jun. 1, 2006, which claims priority to Australian Patent Application No. 2004906783, filed Nov. 29, 2004.

FIELD OF THE INVENTION

THIS INVENTION relates to an isolated protein and encoding nucleic acid suitable for use in Human Cytomegalovirus immunotherapy. In particular, the invention relates to a recombinant protein which includes a polyepitope derived from multiple antigen epitopes conjugated to an extracellular domain of glycoprotein B, which, when used in immunotherapy is capable of eliciting a cytotoxic T-lymphocyte immune response as well as a neutralizing antibody response to Human Cytomegalovirus, without being limited thereto.

BACKGROUND OF THE INVENTION

Human cytomegalovirus (HCMV) belongs to the herpesvirus group and is found universally throughout all geographic locations and socioeconomic groups. While it infects between 50 and 85% of adults, for most healthy persons who acquire primary HCMV after birth, there are no long-term consequences.

However, there are clinical situations where HCMV infection is a significant cause of morbidity and mortality. For example, HCMV infection carries significant health risks to a foetus in utero, to people who work with children, and to individuals having a compromised immune system, eg. those infected with HIV-1 or having undergone organ transplantation (Britt, 1996, Trends Microbio 4 34; Plotkin, 1999, Pediatr Infect Dis J 18 313).

Epidemiological studies have shown that 80 to 90% of developing unborn babies who acquire congenital HCMV infection display a variable pattern of pathological sequelae within the first few years of life that may include hearing loss, vision impairment and mental retardation.

Accordingly, there is a need for an effective vaccine to provide such a reduction in HCMV load within the population. To this end, there have been a number of such attempts using either attenuated HCMV strains or subunit vaccines (as reviewed by Britt, 1996, supra; Plotkin, 1999, supra).

Initial vaccines were based on immunisation using attenuated strains of HCMV, eg., the Towne and AD-169 strains (Elek & Stern, 1974, Lancet 1 1-5, 1974; Neff et al., 1979, Proc Soc Exp Biol Med 160 32). The issue of whether a HCMV vaccine should invoke both humoral and cellular arms of the immune system is of considerable interest and although both attenuated viruses were shown to elicit these responses, neither vaccine prevented foetal infection in pregnant women experiencing a primary HCMV infection. Furthermore, vaccinated normal volunteers showed limited protection from vital challenge using the HCMV Toledo strain (Quinnan et al., 1984, Ann Intern Med 101 478; Alder et al., 1998, Pediatr Infect Dis J. 17 200).

Subsequent vaccine development has included subunit vaccines which are based on single HCMV antigen formulations, eg. by using the full-length glycoprotein B (gB) polypeptide in combination with MF59 adjuvant (Chiron), or alternatively, a recombinant full-length gB polyepitope protein expressed using a viral vector (Pass et al., 1999, J Infect Dis 180 970; Alder et al., 1999, J Infect Dis 180 843). Additionally, a canarypox virus expressing a full length recombinant HCMV pp65 polyepitope has been tested in a clinical trial and shown to elicit a strong CTL and antibody response to this antigen (Gyulai et al., Proceedings of the Seventh International Cytomegalovirus Workshop, Brighton, UK, Mar. 7-9, 1999, abstract). However, vaccine formulations based on one or more full-length HCMV antigens are likely to present a number of limitations in that normal cellular processing is interrupted, thereby affecting epitope presentation. For example, the expression of HCMV proteins such as pp65 can inhibit proteasomal processing of IE-1 through an associated kinase activity (Gilbert et al., 1996, Nature 383, 720).

An alternative approach for producing CTL responses, as described in WO 03/000720, has been to combine a plurality of epitopes from various antigens to form a polyepitope construct and thereby avoid the use of full-length antigens altogether.

SUMMARY OF THE INVENTION

The present invention broadly relates to an isolated protein suitable for use in Human Cytomegalovirus immunotherapy.

In a particular form, the isolated protein comprises a HCMV polyepitope amino acid sequence including a plurality of epitopes from two or more different HCMV antigens and an extracellular Human Cytomegalovirus-encoded glycoprotein B.

The recombinant protein is suitably capable of eliciting both a cytotoxic T-lymphocyte immune response and a humoral immune response (preferably a neutralizing antibody response) to HCMV in a human.

In a first aspect of the invention, there is provided an isolated protein comprising a Human Cytomegalovirus polyepitope amino acid sequence and an amino acid sequence of an extracellular domain of Human Cytomegalovirus glycoprotein B.

Suitably, the Human Cytomegalovirus polyepitope comprises a plurality of epitopes capable of eliciting a cytotoxic T-lymphocyte (CTL) response.

The extracellular domain of Human Cytomegalovirus glycoprotein B may be the entire extracellular domain or a fragment thereof, which comprises one or more B cell epitopes capable of eliciting a neutralizing antibody response.

Suitably, the Human Cytomegalovirus polyepitope comprises epitopes which are selected to provide broad interracial coverage of the human population. In one embodiment, the Human Cytomegalovirus polyepitope comprises a plurality of CTL epitopes restricted by the HLA class I specificities HLA-A1, -A2, -A3, -A11, -A23, -A24, -A26, -A29, -A30, -B7, -B8, -B27, -B35, -B38, -B40, -B41, -B44, -B51, -B57 and -B58.

Preferably, according to this embodiment the epitopes are selected from HCMV antigenic proteins selected from the group consisting of: gB, gH, pp28, pp50, pp65, pp 150, IE-1 and IE-2.

In a preferred embodiment, the Human Cytomegalovirus polyepitope further comprises one or more MHC class II restricted CTL epitopes.

In a particular embodiment, the Human Cytomegalovirus polyepitope comprises a plurality of CTL epitopes selected from Table 1 (SEQ ID NOS: 6-51).

In a preferred form, the Human Cytomegalovirus polyepitope has an amino acid sequence as set forth in FIG. 1 (SEQ ID NO:5).

In embodiments relating to recombinant protein expression in a host cell in vitro, the extracellular domain of Human Cytomegalovirus glycoprotein B includes one or more amino acid substitutions, deletions or additions that remove one or more proteolytic cleavage sites therein.

A non-limiting example is one or more furin proteolytic processing sites in the extracellular domain of Human Cytomegalovirus glycoprotein B.

Even more preferably, the isolated protein further comprises a cytoplasmic domain of glycoprotein B contiguous with the extracellular domain of Human Cytomegalovirus glycoprotein B.

In another particular embodiment, the isolated protein still further comprises a secretion signal amino acid sequence, preferably at the N-terminus of the extracellular domain of Human Cytomegalovirus glycoprotein B.

In particularly preferred embodiments, the isolated protein of this aspect comprises an amino acid sequence as set forth in FIG. 11A (SEQ ID NO:1) or FIG. 12A (SEQ ID NO:2).

In a second aspect, the invention provides an isolated nucleic acid encoding the isolated protein of the first aspect.

In particular embodiments, the isolated nucleic acid may comprise a nucleotide sequence set forth in FIG. 11B (SEQ ID NO: 3) or FIG. 12B (SEQ ID NO: 4), or a fragment thereof.

In a third aspect, the invention provides a genetic construct comprising the isolated nucleic acid of the second aspect.

Preferably, the genetic construct is an expression construct wherein said isolated nucleic acid of the second aspect is operably linked to one or more regulatory sequences present in an expression vector.

In embodiments relating to expression constructs for administration to an animal, the expression vector is preferably a viral vector such as an adenovirus-based expression vector or a pox virus vector, although without limitation thereto.

More preferably, the expression vector is preferably an adenovirus-based expression vector.

Still more preferably, the adenovirus-based expression vector is an Ad5/F35 vector.

In another embodiment, the expression construct comprises an expression vector suitable for production of the isolated protein in vitro as a recombinant protein for subsequent purification.

In a fourth aspect, the invention provides a host cell comprising the expression construct of the third aspect.

In one embodiment, the host cell is a cell isolated from an animal to which the expression construct has been administered.

In another embodiment, the host cell has been transfected, transformed or otherwise introduced with the expression construct in vitro, for the purpose of subsequent purification of the isolated protein of the first aspect.

In a fifth aspect, the present invention provides a pharmaceutical composition comprising an isolated protein of the first aspect, an isolated nucleic acid of the second aspect, or an expression construct of the third aspect and a pharmaceutically-acceptable carrier, diluent or excipient.

Preferably, the pharmaceutical composition is an immunotherapeutic composition suitable for use in the prophylactic or therapeutic treatment of a disease or condition associated with HCMV infection in an animal.

More preferably, the immunotherapeutic composition is a vaccine for eliciting a protective immune response against HCMV.

In a sixth aspect, the invention provides a method of prophylactically or therapeutically treating a Human Cytomegalovirus infection in an animal including the step of administering to the animal an isolated protein of the first aspect, an isolated nucleic acid of the second aspect, or an expression construct of the third aspect.

Preferably, the method includes the step of inducing both cytotoxic T-lymphocyte (CTL) and humoral responses in said animal.

In seventh aspect, the invention provides a method of expanding human CMV-specific CTLs for adoptive immunotherapy, including the steps of:

(i) contacting one or more cells isolated from an animal with the isolated protein of the first aspect; and (ii) culturing said one or more cells to thereby expand HCMV-specific CTLs from said one or more cells.

In an eighth aspect, the invention provides a method of adoptive immunotherapy including the step of administering said HCMV-specific CTLs produced at step (ii) of the seventh aspect to an animal to thereby prophylactically or therapeutically treat a Human Cytomegalovirus infection of said animal.

In a ninth aspect, the invention provides use of the isolated protein of the first aspect or the expression construct of the third aspect in the manufacture of a medicament for prophylactically or therapeutically treating a Human Cytomegalovirus infection in an animal.

Preferably, according to the aforementioned aspects the animal is a mammal.

More preferably, the animal is a primate.

Even more preferably, the animal is a human.

Throughout this specification, unless otherwise indicated, “comprise”, “comprises” and “comprising” are used inclusively rather than exclusively, so that a stated integer or group of integers may include one or more other non-stated integers or groups of integers.

BRIEF DESCRIPTION OF THE FIGURES

In order that the present invention may be more readily understood and placed into practical effect, preferred embodiments of the invention will be described, by way of example only, with reference to the accompanying figures.

FIG. 1: Schematic representation of synthesis of AdCMVpoly construct.

FIG. 2: Data showing that the recombinant protein is efficiently recognized by the gB-specific monoclonal antibody.

FIG. 3: Data showing that the gB-specific antibody efficiently captures the recombinant protein.

FIG. 4: Representative data from two different human donors showing activation of multiple epitope-specific CTL activation following incubation with the recombinant protein.

FIG. 5: SDS-PAGE gel of resolved gB-CMV polyepitope protein and HCMV virus extract showing the molecular weight of the recombinant protein.

FIG. 6: Data showing that the Human Cytomegalovirus polyepitope is highly efficient in recalling multiple CTL responses which were specific for the epitopes restricted by the HLA alleles expressed by each donor.

FIG. 7: Studies showing moderate levels of T cell responses to selected epitopes following immunization with three different vectors.

FIG. 8: Studies showing enhanced T cell responses following a single immunization with $10^{10}$ PFU/mice.

FIG. 9: Analysis of gB-specific antibody response in serum samples from mice immunized with AdSig-gB-CMVpoly, AdgBCMV poly, control adenovirus or medium alone using ELISA assay.

FIG. 10: (A) Data from mice immunized with Sig-gB-CMVpoly construct showing gB-specific antibody response and (B) test of serum samples shows significant neutralizing activity in mice immunized with Sig-gBCMVpoly when compared to control mice (mock immunized with control adenovirus).

FIG. 11: (A) Amino acid sequence of an isolated protein for adenoviral expression in an animal; and (B) encoding nucleotide sequence.

FIG. 12: (A) Amino acid sequence of an isolated protein for recombinant protein expression in a host cell in vitro; and (B) encoding nucleotide sequence.

BRIEF DESCRIPTION OF THE SEQUENCE LISTING

SEQ ID NO:1: Amino acid sequence of an isolated protein for adenoviral expression in an animal (FIG. 11A).
SEQ ID NO:2: Amino acid sequence of an isolated protein for recombinant protein expression in a host cell in vitro (FIG. 12A).
SEQ ID NO:3: Nucleotide sequence encoding SEQ ID NO:1 (FIG. 11B).
SEQ ID NO:4: Nucleotide sequence encoding SEQ ID NO:2 (FIG. 12B).
SEQ ID NO:5: Amino acid sequence of a HCMV polyepitope (FIG. 1).
SEQ ID NOS:6-49: Amino acid sequences of HLA Class I-restricted CTL epitopes used in HCMV polyepitope (Table 1).
SEQ ID NO:50 & 51: Amino acid sequences of HLA Class II-restricted CTL epitopes used in HCMV polyepitope (respectively HELLVLVKKAQL and DDYSNTHSTRYV in Table 1).
SEQ ID NOS: 52-54: Nucleotide sequences of gB oligonucleotides (Table 5).
SEQ ID NOS: 55-77: Nucleotide sequences of HCMV polyepitope oligonucleotides (Table 5).
SEQ ID NOS: 78-87: Nucleotide sequences of oligonucleotides for the construction of expression vectors for production of protein in mammalian cells (Table 6).

DETAILED DESCRIPTION OF THE PREFERRED EMBODIMENTS

The invention provides an isolated protein comprising a Human Cytomegalovirus (HCMV) polyepitope which includes a plurality of cytotoxic T-lymphocyte (CTL) epitopes from two or more different HCMV-derived antigenic proteins together with an extracellular domain of HCMV glycoprotein B for eliciting a humoral (e.g. neutralizing antibody) immune response.

More particularly, the invention provides an isolated protein, pharmaceutical compositions and methods for treatment of HCMV-associated diseases and conditions that stimulate both CTL and humoral (e.g. neutralizing antibody) responses.

A particular feature of the present invention is that the isolated protein of the invention is a single, contiguous construct comprising a HCMV polyepitope sequence that elicits a strong CTL response and an extracellular domain of a gB glycoprotein that elicits a neutralizing antibody response.

This single, contiguous construct and a nucleic acid encoding same, is expected to be more convenient and useful for the preparation of immunotherapeutic compositions administrable to primates, particularly humans, for the treatment of diseases and conditions associated with HCMV infection.

This efficacy is unexpected given the expectation that a single, contiguous protein comprising an extracellular domain of glycoprotein B and a HCMV polytope in a highly artificial context might undergo incorrect folding and cellular processing, resulting in inadequate or faulty antigen presentation. Indeed the present inventors have surprisingly shown that each of the polyepitope and glycoprotein B components are efficiently processed by human cells for display to the immune system and that strong T cell responses are induced when HLA class I transgenic mice are immunised with this vaccine.

Significantly and surprisingly, the gB extracellular domain in the context of this single, contiguous protein, elicited a neutralizing antibody response notwithstanding the high probability that incorrect folding may have compromised the immunogenicity of the B cell epitopes present in the gB extracellular domain.

In one aspect, the invention provides an isolated protein comprising a Human Cytomegalovirus polyepitope ("HCMV polyepitope") amino acid sequence and an amino acid sequence of an extracellular domain of Human Cytomegalovirus glycoprotein B ("HCMV gB").

The isolated protein may be herein referred to as "gB-CMV polyepitope" or more specifically "Sig-gB-CMV polyepitope" in cases where an N-terminal signal peptide sequence is present.

The N-terminal signal sequence may be a native gB signal sequence (e.g. residues 2-30 of gB) or a tPA signal sequence.

For the purposes of this invention, by "isolated" is meant material that has been removed from its natural state or otherwise been subjected to human manipulation. Isolated material may be substantially or essentially free from components that normally accompany it in its natural state, or may be manipulated so as to be in an artificial state together with components that normally accompany it in its natural state.

By "protein" is meant an amino acid polymer comprising natural and/or non-natural amino acids, D- or L-amino acids as are well known in the art.

A "peptide" is a protein having no more than fifty (50) amino acids.

A "polypeptide" is a protein having more than fifty (50) amino acids.

The HCMV polyepitope preferably comprises a plurality of HCMV CTL epitopes derived from a plurality of different HCMV protein antigens.

In particular embodiments, the plurality of different HCMV protein antigens are selected from the group consisting of: gB, gH, pp28, pp50, pp65, pp 150, IE-1 and IE-2.

Preferably, the HCMV polyepitope comprises one or more HCMV CTL epitopes derived from each of gB, gH, pp28, pp50, pp65, pp 150, IE-1 and IE-2.

Each of the HCMV antigens were selected according to their particular properties. The viral glycoproteins gB and gH were chosen because they appear to be involved in virus attachment, whereas the IE-1 and IE-2 proteins are expressed during viral replication. IE-1 and IE-2 are considered to be important for viral reactivation and to play a role in HCMV-induced pathology. The phosphoproteins (pp28, pp50, pp65, and pp 150) are all tegument proteins. The present inventors reason that by priming the immune response to these antigens, viral replication may be controlled at the level of attachment, replication, assembly and reactivation from the latent phase, all of which are all crucial stages of HCMV infection.

The epitopes were selected to cover the HLA-A1, -A2, -A3, -A11, -A23, -A24, -A26, -A29, -A30, -B7, -B8, -B27, -B35, -B38, -B40, -B41, -B44, -B51, -B57, -B58 specificities which are predicted to provide ca. 97 to 98% coverage of the US human population.

However, it will be appreciated by a skilled person that epitope selected may be tailored to fit any population, irrespective of race. This percentage of individuals is expected to respond to at least one epitope in the array.

In a preferred form, also included are two HLA class II-restricted epitopes (SEQ ID NOS: 50 & 51).

Other criteria for inclusion within the polyepitope include those (i) having minimal or no sequence variants; (ii) selected from HLAs having minimal subtypes; (iii) having a high frequency of CTL responses in healthy HCMV seropositives; and (iv) based on epitope hydrophobic properties, wherein the novel sequential order of individual epitopes are arranged such that hydrophobicity is uniform distributed along the length of the polyepitope to assist inter cellular mobility.

A non-limiting example of HCMV CTL epitopes useful in a HCMV polyepitope according to the invention is provided in Table 1 (SEQ ID NOS: 6-51).

A preferred HCMV polyepitope sequence is set forth in SEQ ID NO:5 (FIG. 1).

However, it will also be appreciated that other HCMV CTL epitopes may be used, such as described in International Application WO 03/000720.

Furthermore, it will be appreciated that the particular number and order of the constituent CTL epitopes may readily be altered while retaining broad HLA Class I and/or Class II restriction and immunogenicity.

The HCMV polyepitope set forth in SEQ ID NO:5 and FIG. 1 consists of a plurality of CTL epitopes, in that there are no additional amino acid residues flanking each CTL epitope.

However, it will be appreciated by the skilled person that additional amino acids may be included without adversely affecting HCMV polyepitope immunogenicity.

For example, the HCMV polyepitope may "consist essentially of" a plurality of HCMV CTL epitopes.

By "consist essentially of" is meant that no more than 1, 2 or 3 additional amino acids are present at an N- and/or C-terminus of one or more of the HCMV CTL epitopes.

Preferably, in embodiments where there are additional residues, the additional amino acids present in the polyepitope are amino acids that do not naturally flank the constituent epitopes present in native HCMV protein antigens.

In addition to the HCMV polyepitope, the isolated gB-CMV polyepitope protein of the invention further comprises a gB extracellular domain, or a fragment of the extracellular domain, comprising one or more B epitopes capable of eliciting a neutralizing antibody response.

Substantially the entire extracellular domain of gB is found within or corresponds to residues 31-700 of gB.

The native gB signal sequence is residues 2-30 of gB,

In embodiments where the isolated protein is to be produced in a host cell in vitro, the extracellular domain of Human Cytomegalovirus glycoprotein B preferably includes one or more amino acid substitutions, deletions or additions that remove one or more proteolytic cleavage sites therein.

A non-limiting example is one or more furin proteolytic processing sites in the extracellular domain of Human Cytomegalovirus glycoprotein B.

In particular embodiments, the one or more amino acid substitutions, deletions or additions are selected from the group consisting of: $Arg_{433}$ to $Gln_{433}$, $Arg_{435}$ to $Thr_{435}$ and $Arg_{436}$ to $Gln_{436}$.

In embodiments relating to recombinant protein expression in a host cell in vitro, the isolated protein may further comprise a gB intracellular domain contiguous with the gB extracellular domain.

In this regard, the isolated protein of the invention may be a Sig-gB-CMV polyepitope protein which comprises a secretion signal sequence.

In one embodiment, a native, gB secretion signal sequence may be included at the N-terminus of a gB-HCMV polyepitope construct resulting in increased activity compared to a construct without the signal sequence.

In another embodiment particularly suited to recombinant protein expression in a host cell in vitro, a tPA signal sequence may be included at the N-terminus of a gB-HCMV polyepitope construct in place of a native gB signal sequence.

It will also be appreciated that the isolated protein described herein may be subjected to further modifications, variations and/or derivitizations without departing from the inventive concept.

Variations in amino acid sequence may be the result of naturally occurring sequence variation in a gB and/or HCMV polyepitope and/or signal peptide sequence.

Alternatively, the invention contemplates isolated proteins which vary from those exemplified herein such as by addition, deletion or substitution of amino acid residues in the gB and/or HCMV polyepitope and/or signal peptide sequences exemplified herein.

It is well understood in the art that some amino acids may be changed to others with broadly similar properties without changing the nature of the activity of the isolated protein (conservative substitutions).

Typically, conservative substitutions are made so that amino acid properties such as charge, hydrophilicity, hydrophobicity and/or side chain size or "bulkiness" are retained or at least minimally altered.

Generally, although not exclusively, amino acid substitutions which are likely to produce the greatest changes in protein structure and/or function are those in which a hydrophilic residue is substituted for, or by, a hydrophobic residue a cysteine or proline is substituted for, or by, any other residue; a residue having a positive charge is substituted for, or by, a negative charge or a residue having a bulky side chain is substituted for, or by, one having a smaller side chain) or no side chain.

Introduction of amino acid substitutions may be readily achieved during peptide synthesis or during synthesis of an encoding nucleic acid. Other techniques include chemical mutagenesis of an isolated protein or mutagenesis of an encoding nucleic acid.

Non-limiting examples of nucleic acid mutagenesis methods are provided in Chapter 9 of CURRENT PROTOCOLS IN MOLECULAR BIOLOGY, Ausubel et al., supra, Stemmer, 1994, Proc. Natl. Acad. Sci. USA 91 10747, Shafikhani et al., 1997, Biotechniques 23 304, Jenkins et al., 1995, EMBO J. 14 4276-4287 and Zaccolo et al., 1996, J. Mol. Biol. 255 589.

More particularly, site-directed mutagenesis may be performed using a commercially available kit, for example QuickChange™ Site-Directed Mutagenesis Kit from Stratagene.

Random mutagenesis kits are also commercially available, such as the Diversify™ random mutagenesis kit (Clontech).

Generally, the invention contemplates protein variants having at least 75%, preferably at least 80%, more preferably at least 85% or even more preferably at least 90, 91, 92, 93, 94, 95, 96, 97, 98 or 99% amino acid sequence identity with SEQ ID NO:1, SEQ ID NO:2, or with the constituent gB and/or HCMV polytope (such as SEQ ID NO:5) or signal peptide sequences therein.

Such levels of sequence identity may readily be determined by sequence analysis algorithms such as ClustalW or BlastP as are well understood in the art.

As used herein, "derivative" proteins of the invention have been altered, for example by conjugation, fusion with additional protein sequences, by complexing with other chemical moieties or by post-translational modification techniques as would be understood in the art.

"Additions" of amino acids may include fusion with amino acid sequences of other proteins such as "fusion partners" or "epitope tags" which assist recombinant protein purification and/or identification.

Well known examples of fusion partners include, but are not limited to, glutathione-S-transferase (GST), Fc portion of human IgG, maltose binding protein (MBP) and hexahistidine ($HIS_6$), which are particularly useful for isolation of the fusion polypeptide by affinity chromatography. For the purposes of fusion protein purification by affinity chromatography, relevant matrices for affinity chromatography are glutathione-, amylose-, and nickel- or cobalt-conjugated resins respectively. Many such matrices are available in "kit" form, such as the QIAexpress™ system (Qiagen) useful with ($HIS_6$) fusion partners and the Pharmacia GST purification system.

Another fusion partner well known in the art is green fluorescent protein (GFP). This fusion partner serves as a fluorescent "tag" which allows the fusion protein of the invention to be identified by fluorescence microscopy or by flow cytometry. The GFP tag is useful when assessing subcellular localization of the fusion polypeptide of the invention, or for isolating cells which express the fusion polypeptide of the invention. Flow cytometric methods such as fluorescence activated cell sorting (FACS) are particularly useful in this latter application.

Preferably, the fusion partners also have protease cleavage sites, such as for Factor $X_a$ or Thrombin, which allow the relevant protease to partially digest the fusion protein of the invention and thereby liberate the recombinant protein of the invention therefrom. The liberated protein can then be isolated from the fusion partner by subsequent chromatographic separation.

Fusion partners according to the invention also include within their scope "epitope tags", which are usually short sequences for which a specific antibody is available. Well-known examples of epitope tags for which specific monoclonal antibodies are readily available include c-myc, influenza virus haemagglutinin and FLAG tags.

Other derivatives contemplated by the invention include, but are not limited to, modification to side chains, incorporation of unnatural amino acids and/or their derivatives during peptide, polypeptide or protein synthesis and the use of crosslinkers and other methods which impose conformational constraints on the isolated protein of the invention. Examples of side chain modifications contemplated by the present invention include modifications of amino groups such as by acylation with acetic anhydride; acylation of amino groups with succinic anhydride and tetrahydrophthalic anhydride; amidination with methylacetimidate; carbamoylation of amino groups with cyanate; pyridoxylation of lysine with pyridoxal-5-phosphate followed by reduction with $NaBH_4$; reductive alkylation by reaction with an aldehyde followed by reduction with $NaBH_4$; and trinitrobenzylation of amino groups with 2,4,6-trinitrobenzene sulfonic acid (TNBS).

The carboxyl group may be modified by carbodiimide activation via O-acylisourea formation followed by subsequent derivitization, by way of example, to a corresponding amide.

The guanidine group of arginine residues may be modified by formation of heterocyclic condensation products with reagents such as 2,3-butanedione, phenylglyoxal and glyoxal.

Sulfhydryl groups may be modified by methods such as performic acid oxidation to cysteic acid; formation of mercurial derivatives using 4-chloromercuriphenylsulfonic acid, 4-chloromercuribenzoate; 2-chloromercuri-4-nitrophenol, phenylmercury chloride, and other mercurials; formation of a mixed disulfides with other thiol compounds; reaction with maleimide, maleic anhydride or other substituted maleimide; carboxymethylation with iodoacetic acid or iodoacetamide; and carbamoylation with cyanate at alkaline pH.

Tryptophan residues may be modified, for example, by alkylation of the indole ring with 2-hydroxy-5-nitrobenzyl bromide or sulfonyl halides or by oxidation with N-bromo-succinimide.

Tyrosine residues may be modified by nitration with tetranitromethane to form a 3-nitrotyrosine derivative.

The imidazole ring of a histidine residue may be modified by alkylation with iodoacetic acid derivatives.

Examples of incorporating unnatural amino acids and derivatives during peptide synthesis include but are not limited to, use of 4-amino butyric acid, 6-aminohexanoic acid, 4-amino-3-hydroxy-5-phenylpentanoic acid, 4-amino-3-hydroxy-6-methylheptanoic acid, t-butylglycine, norleucine, norvaline, phenylglycine, ornithine, sarcosine, 2-thienyl alanine and/or D-isomers of amino acids.

Typically, proteins may be produced by recombinant DNA technology or by chemical synthesis, inclusive of solid phase and solution phase synthesis. Such methods are well known in the art, although reference is made to examples of chemical synthesis techniques as provided in Chapter 9 of SYNTHETIC VACCINES Ed. Nicholson (Blackwell Scientific Publications) and Chapter 15 of CURRENT PROTOCOLS IN PROTEIN SCIENCE Eds. Coligan et al., (John Wiley & Sons, Inc. NY USA 1995-2001).

Recombinant proteins may be conveniently prepared by a person skilled in the art using standard protocols as for example described in Sambrook et al., MOLECULAR CLONING. A Laboratory Manual (Cold Spring Harbor Press, 1989), in particular Sections 16 and 17; CURRENT PROTOCOLS IN MOLECULAR BIOLOGY Eds. Ausubel et al., (John Wiley & Sons, Inc. NY USA 1995-2001), in particular Chapters 10 and 16; and CURRENT PROTOCOLS IN PROTEIN SCIENCE Eds. Coligan et al., (John Wiley & Sons, Inc. NY USA 1995-2001, in particular Chapters 1, 5 and 6.

In another aspect, the invention provides an isolated nucleic acid encoding the aforementioned isolated protein of the invention.

The isolated nucleic acid of the invention may be useful for recombinant protein expression in vivo in an animal, or in a host cell for the purposes of subsequent recombinant protein purification.

An example of a nucleotide sequence of an isolated nucleic acid encoding an isolated protein of the invention for adenoviral expression in an animal is provided in FIG. 11B (SEQ ID NO:3)

An example of a nucleotide sequence of an isolated nucleic acid encoding an isolated protein of the invention for recombinant protein expression in a host cell in vitro is provided in FIG. 12B (SEQ ID NO:4).

It will be appreciated by persons skilled in the art that advantage may be taken of degeneracy in the genetic code to alter an encoding nucleotide sequence of an amino acid sequence.

In a particular example, a nucleotide sequence may be engineered according to codon preference or usage in an organism or cell type to thereby optimize encoded protein translation and expression in that organism or cell type.

The term "nucleic acid" as used herein designates single- or double-stranded mRNA, RNA, cRNA and DNA, said DNA inclusive of cDNA and genomic DNA.

Nucleic acids may comprise genetically-encoded bases such as adenine, guanine, cytosine, thymine and uracil, or modified bases such as inosine, methylinosine and methyladenosine, thiouridine and methylcytosine, although without limitation thereto.

The term "recombinant" as used herein means artificially produced through human manipulation of genetic material, such as involving techniques generally falling within the scope of "recombinant DNA technology" as is well understood in the art.

A "polynucleotide" is a nucleic acid having eighty (80) or more contiguous nucleotides, while an "oligonucleotide" has less than eighty (80) contiguous nucleotides.

A "probe" may be a single or double-stranded oligonucleotide or polynucleotide, suitably labelled for the purpose of detecting complementary sequences in Northern or Southern blotting, for example.

A "primer" is usually a single-stranded oligonucleotide, preferably having 15-50 contiguous nucleotides, which is capable of annealing to a complementary nucleic acid "template" and being extended in a template-dependent fashion by the action of a DNA polymerase such as Taq polymerase, RNA-dependent DNA polymerase or Sequenase™.

An "amplification product" refers to a nucleic acid product generated by nucleic acid amplification techniques.

Also contemplated according to the present invention are isolated nucleic acids that encode variants and/or derivatives of the isolated protein as hereinbefore described.

Typically, such isolated nucleic acids that encode variant proteins of the invention will hybridize with SEQ ID NO:3 or SEQ ID NO:4 under high stringency wash conditions.

High stringency conditions include and encompass:
(i) from at least about 31% v/v to at least about 50% v/v formamide and from at least about 0.01 M to at least about 0.15 M salt for hybridisation at 42° C., and at least about 0.01 M to at least about 0.15 M salt for washing at 42° C.;
(ii) 1% BSA, 1 mM EDTA, 0.5 M NaHPO$_4$ (pH 7.2), 7% SDS for hybridization at 65° C., and (a) 0.1×SSC, 0.1% SDS; or (b) 0.5% BSA, 1 mM EDTA, 40 mM NaHPO$_4$ (pH 7.2), 1% SDS for washing at a temperature in excess of 65° C. for about one hour; and
(iii) 0.2×SSC, 0.1% SDS for washing at or above 68° C. for about 20 minutes.

As hereinbefore described, the invention provides a genetic construct comprising an isolated nucleic acid of the invention.

The genetic construct may facilitate propagation, cloning and/or expression of the isolated nucleic acid.

In a preferred form, the genetic construct is an expression construct comprising an isolated nucleic acid of the invention operably linked to one or more regulatory sequences present in an expression vector.

An "expression vector" may be either a self-replicating extra-chromosomal vector such as a plasmid, or a vector that integrates into a host genome. Suitably, the expression vector provides said one or more regulatory nucleotide sequences. By "operably linked" is meant that said regulatory nucleotide sequence(s) is/are positioned relative to the recombinant nucleic acid of the invention to initiate, regulate or otherwise control transcription.

Regulatory nucleotide sequences will generally be appropriate for the host cell used for expression. Numerous types of appropriate expression vectors and suitable regulatory sequences are known in the art for a variety of host cells.

Typically, said one or more regulatory nucleotide sequences may include, but are not limited to, promoter sequences, leader or signal sequences, ribosomal binding sites, transcriptional start and termination sequences, translational start and termination sequences, and silencer, enhancer or activator sequences.

With regard to promoters, constitutive promoters (such as CMV, SV40, vaccinia, HTLV1 and human elongation factor promoters) and inducible/repressible promoters (such as tet-repressible promoters and IPTG-, metallothionin- or ecdys-one-inducible promoters) are well known in the art and are contemplated by the invention. It will also be appreciated that promoters may be hybrid promoters that combine elements of more than one promoter, such as but not limited to the SRα promoter which is a hybrid between elements of HTLV1 and SV40 promoters.

Preferably, said expression construct also includes one or more selectable markers suitable for the purposes of selection of transformed bacteria (such as bla, kanR and tetR) or transformed mammalian cells (such as hygromycin, G418 and puromycin).

Expression constructs may be transfected, transformed or otherwise introduced into host cells by any of a number of well known techniques including, but not limited to, transformation by heat shock, electroporation, DEAE-Dextran transfection, microinjection, liposome-mediated transfection, calcium phosphate precipitation, protoplast fusion, microparticle bombardment, viral transformation and the like.

The expression vector may also include a fusion partner (as hereinbefore described and typically provided by the expression vector) so that the recombinant protein of the invention is expressed as a fusion polypeptide with said fusion partner. The main advantage of fusion partners is that they assist identification and/or purification of said fusion polypeptide.

In embodiments relating to production of a recombinant gB-CMV polyepitope protein or Sig-gB polyepitope protein, the recombinant protein may be prepared by a procedure including the steps of:
(i) preparing an expression construct which comprises an isolated nucleic acid encoding the gB-CMV polyepitope protein or Sig-gB polyepitope protein, operably linked to one or more regulatory nucleotide sequences;
(ii) transfecting, transforming or otherwise introducing the expression construct into a suitable host cell;
(iii) expressing the recombinant protein in said host cell; and
(iv) purifying the recombinant protein.

The conditions appropriate for protein expression will vary with the choice of expression vector and the host cell. This is easily ascertained by one skilled in the art through routine experimentation.

Suitable host cells for expression may be prokaryotic or eukaryotic, such as *Escherichia coli* (DH5α for example), yeast cells, Sf9 cells utilized with a baculovirus expression system, mammalian cell lines such as human embryonic kidney (HEK) 293 cells, CHO cells, COS cells, CV1 cells, Jurkat and NIH3T3 cells although without limitation thereto.

Preferably, the host cell is a human embryonic kidney (HEK) 293 cell stably transfected with an expression construct of the invention comprising one or more regulatory sequences (e.g. a promoter) operable in a mammalian cell.

In embodiments relating to expression constructs for administration to animals such as primates and particularly humans, the expression construct of the invention is suitable for use as a DNA vaccine.

In particular forms, the expression construct of the invention may be a construct that utilizes an expression and delivery vector of viral origin, such as pox viruses and adenoviruses.

When used as a vaccine delivery system, expression constructs of viral origin may be administered to an animal in the form of VLPs or as a "naked" nucleic acid construct.

In one particular embodiment, the expression construct according to this embodiment comprises a vaccinia virus promoter, such as the p7.5 promoter present in a plasmid vector. For example, production of a TK-recombinant vaccinia virus using marker rescue recombination as provided in Khanna et al., 1992. J Exp Med. 176 169.

In a more preferred embodiment, the invention provides an adenovirus-based expression construct for use in a vaccine delivery system. Adenovirus-based constructs are capable of infecting a broad spectrum of mammalian and human cells, including both quiescent and proliferating cell types.

Such adenovirus-based expression constructs may comprise a constitutive or inducible/repressible promoter such as by way of a tetracycline inducible/repressible system.

A preferred form of the adenovirus-based expression construct is derived from a replication-incompetent A5 adenovirus lacking at least an E1 gene.

A particularly preferred form is the Ad5/F35 adenovirus-based expression construct and vaccine delivery system is provided in detail hereinafter. Reference is also made to Yotdna et al., 2001, Gene Therapy 8 930, in relation to the Ad5/F35 embodiment of adenovirus expression vectors.

Pharmaceutical Compositions and Therapeutic Uses

It will be appreciated that the isolated protein of the invention, isolated nucleic acids and expression constructs encoding same may be useful in therapeutic and/or prophylactic treatment of a Human Cytomegalovirus-associated disease and/or condition in an animal.

Preferably, the animal is a primate, such as a human. In humans, HCMV infection can cause a mononucleosis-like syndrome with prolonged fever, and/or a mild hepatitis. In certain high-risk groups, disease can be more severe, such as during infection of the unborn baby during pregnancy, in people who work with children, and in immunocompromised persons, such as the aged, organ transplant recipients and persons infected with human immunodeficiency virus (HIV).

The invention therefore provides pharmaceutical compositions and/or methods of prophylactic or therapeutic treatment of HCMV infection, preferably in human.

Such pharmaceutical compositions and methods are suitable for delivery of the isolated protein in recombinant form, or encoded by an expression construct (preferably in a viral delivery vector).

Suitably, pharmaceutical compositions further comprise a pharmaceutically-acceptable carrier, diluent or excipient.

By "pharmaceutically-acceptable carrier, diluent or excipient" is meant a solid or liquid filler, diluent or encapsulating substance that may be safely used in systemic administration. Depending upon the particular route of administration, a variety of carriers, well known in the art may be used. These carriers may be selected from a group including sugars, starches, cellulose and its derivatives, malt, gelatine, talc, calcium sulfate, vegetable oils, synthetic oils, polyols, alginic acid, phosphate buffered solutions, emulsifiers, isotonic saline and salts such as mineral acid salts including hydrochlorides, bromides and sulfates, organic acids such as acetates, propionates and malonates and pyrogen-free water.

A useful reference describing pharmaceutically acceptable carriers, diluents and excipients is Remington's Pharmaceutical Sciences (Mack Publishing Co. N.J. USA, 1991) which is incorporated herein by reference.

Any safe route of administration may be employed for providing a patient with the composition of the invention. For example, oral, rectal, parenteral, sublingual, buccal, intravenous, intra-articular, intramuscular, intra-dermal, subcutaneous, inhalational, intraocular, intraperitoneal, intracerebroventricular and transdermal administration may be employed.

Dosage forms include tablets, dispersions, suspensions, injections, solutions, syrups, troches, capsules, suppositories, aerosols, transdermal patches and the like. These dosage forms may also include injecting or implanting controlled releasing devices designed specifically for this purpose or other forms of implants modified to act additionally in this fashion. Controlled release of the therapeutic agent may be effected by coating the same, for example, with hydrophobic polymers including acrylic resins, waxes, higher aliphatic alcohols, polylactic and polyglycolic acids and certain cellulose derivatives such as hydroxypropylmethyl cellulose. In addition, the controlled release may be effected by using other polymer matrices, liposomes and/or microspheres.

In a particular embodiment relating to adenoviral delivery and expression for therapeutic purposes, the invention provides a pharmaceutical composition comprising an expression construct that encodes a Sig-gB-CMV polytope protein.

Preferred pharmaceutical compositions are "immunotherapeutic or immunogenic compositions" that provide prophylactic and/or therapeutic treatment of HCMV responsive to such immunotherapy, without necessarily eliciting a protective immune response.

In a preferred form, the immunotherapeutic composition may be a vaccine for eliciting a protective immune response in a human subject against HCMV wherein the vaccine comprises the isolated protein of the first aspect or the expression construct of the third aspect in combination with a pharmaceutically-acceptable carrier, diluent or excipient.

In embodiments relating to administration of a vaccine in the form of an expression construct, the invention provides a nucleic acid vaccine, inclusive of DNA vaccines as are understood in the art.

In this regard, the invention also provides a vaccine that comprises an expression construct that utilizes a viral vector such as an adenoviral vector or pox virus-derived vector as hereinbefore described.

Any suitable procedure is contemplated for producing such vaccines. Exemplary procedures include, eg., those described in New Generation Vaccines (1997, Levine et al., Marcel Dekker, Inc. New York, Basel, Hong Kong) which is incorporated herein by reference.

The immunotherapeutic compositions and vaccines of the invention may include an "immunologically-acceptable carrier, diluent or excipient".

The "immunologically-acceptable carrier, diluent or excipient" includes within its scope water, bicarbonate buffer, phosphate buffered saline or saline and/or an adjuvant as is well known in the art. Suitable adjuvants include, but are not limited to: surface active substances such as hexadecylamine, octadecylamine, octadecyl amino acid esters, lysolecithin, dimethyldioctadecylammonium bromide, N,N-dicoctadecyl-N',N'bis(2-hydroxyethyl-propanediamine), methoxyhexadecylglycerol, and pluronic polyols; polyamines such as pyran, dextransulfate, poly IC carbopol; peptides such as muramyl dipeptide and derivatives, dimethylglycine, tuftsin; oil emulsions; and mineral gels such as aluminum phosphate, aluminum hydroxide or alum; lymphokines, QuilA and immune stimulating complexes (ISCOMS).

In a preferred form, immunotherapeutic compositions and vaccines of the invention comprise the isolated protein of the invention formulated in ISCOMS.

Generally, with regard to pharmaceutical compostions, immunotherapeutic compositions and/or vaccines, any safe route of administration may be employed for providing a patient with the composition of the invention. For example, oral, rectal, parenteral, sublingual, buccal, intravenous, intra-articular, intra-muscular, intra-dermal, subcutaneous, inhalational, intraocular, intraperitoneal, intracerebroventricular, transdermal and the like may be employed. Intra-muscular and subcutaneous injection is appropriate, for example, for administration of immunogenic compositions, proteinacious vaccines and DNA vaccines.

With regard to methods of treatment of HCMV infection and/or a disease or condition associated with, or resultant from HCMV infection, the invention contemplates adoptive immunotherapy.

Preferably, although not exclusively, the invention contemplated adoptive immunotherapy using autologous CTLs produced in vitro.

Current methods for expanding HCMV CTLs are very difficult and are often based on either using a HCMV lysate or individual peptide epitopes. The isolated protein of the invention is expected to be more advantageous than either of these prior art approaches by facilitating expansion of broadly focussed T cell responses.

In one embodiment, the invention provides a method of autologous adoptive immunotherapy in a human including the steps of:

(A) contacting one or more cells isolated from a human with an isolated gB-CMV polyepitope protein or a Sig-gB-CMV polyepitope protein;

(B) culturing said one or more cells to thereby expand HCMV-specific CTL from said one or more cells; and (C) administering said HCMV-specific CTLs to said human to thereby prophylactically or therapeutically treat a Human Cytomegalovirus infection of said animal.

In order that the invention may be readily understood and put into practical effect, particular embodiments will now be described by way of the following non-limiting examples.

EXAMPLES

Example 1

HCMV Adenoviral Expression Constructs

Construction of a gB Vector with and without a Signal Sequence

HCMV encoded glycoprotein B (gB) was amplified from AD 169 virus stock by PCR using gene specific primers (pgBSIGF, pgBNOSIGF and pgBR) as shown in Table 5. The 5' primer included a Bam H1 restriction site followed by a Kozak sequence and start codon. The 3' primer included a Hind III restriction site. Two constructs were made, the first coding from the start methionine at position 2 to valine at position 700 thereby incorporating the signal sequence and the second coding from the alanine at position 31 to valine at position 700 with the deletion of the signal sequence. Following amplification, the DNA was gel purified, cloned into pBluescript 11 KS+ phagemid (Stratagene) and confirmed by DNA sequence analysis.

Recombinant CMV Polyepitope Construction

The epitopes have been combined using 'Polytope' technology as described in WO 03/000720. The amino acid sequence of the 38 contiguous HLA class I-restricted CTL epitopes of Table 1 was translated to the nucleotide sequence using human universal codon usage. Fifteen oligonucleotides (HCMV1a-12 in the range of 102-107 mer as defined in Table 5) overlapping by 20 base pairs and representing the polyepitope DNA sequence, were annealed together by using Splicing by Overlap Extension and stepwise asymmetric PCR (as schematically represented in FIG. 1). Briefly, polyepitope sequence specific primers HCMV 1a and HCMV Ic were annealed, extended and amplified by PCR for 5 cycles in a 20 μL reaction volume containing Elongase enzyme mix (Invitrogen, Australia) PCR buffers and dNTPs. At the end of 5 cycles, the PCR program was paused at 72 C, 2 μL of reaction was transferred to a new 20 μL reaction and subjected to a further 5 cycles with primer HCMV 2 and the polyepitope sequence specific forward primer. This stepwise PCR was repeated until all oligonucleotides were joined. In the final step, 2 μL of the last reaction was amplified for 25 cycles using polyepitope sequence specific forward and reverse primers.

The nucleic acid sequence of the final fragment coded for an EcoR I restriction site, a start codon, 38 contiguous minimal CMV CTL epitopes, followed by a Hind III restriction site. The full-length gel purified PCR fragment was cloned into the EcoR I/Hind III site of pBluescript II KS+ phagemid and was confirmed by DNA sequence analysis.

An additional 8 contiguous HLA class I restricted CTL epitopes were added to the above construct using Splicing by Overlap Extension and stepwise asymmetric PCR involving oligonucleotides extP1 to extP3 as described above. The final PCR fragment was cloned into the Cla I/Xho I site of pBluescript II KS+ phagemid and confirmed by DNA sequence analysis. The original construct encoding the 38 contiguous HLA class I restricted CTL epitopes was then re-cloned into the Eco RI/Hind III restriction sites of this construct, resulting in a final construct containing 46 CTL epitopes.

The final CMV polyepitope was coded for an Eco RI restriction site, a Kozak sequence, 38 contiguous HLA class I restricted CTL epitopes, a Hind III site, a ClaI site, 8 additional epitopes and a Xho I restriction site.

Construction of gB-CMV Polytope Vectors

The recombinant CMV polytope construct insert was excised from the pBluescript II KS+ phagemid using the Eco RI/Xho I restriction enzymes, cloned into the gB pBluescript vectors and confirmed by DNA sequence analysis. The final constructs are shown below and summarized in Table 2.

Construction of Recombinant Ad5F35 Vectors

The adenovirus-based expression vector AD5/F35 allows highly efficient transduction of professional antigen presenting cells in vitro and in vivo. The assembly and production of the recombinant Ad5F35-based adenovirus was completed in three stages using a highly efficient, ligation-based protocol (Mizuguchi & Kay, 1998, Hum. Gene Ther., 9 2577; Mizuguchi & Kay, 1999, Hum. Gene Ther., 10 2013) of the Adeno-X System (CLONTECH, Palo Alto, Calif.) (FIG. 1).

Firstly, inserts were excised from each of four constructs (1, 2, 4 and 5 in Table 2) in pBluescript II KS+ phagemid using Xba I/Kpn I restriction enzymes and cloned into the pShuttle expression vector which contains a stop codon following the cloning sites in the three open reading frames. Following amplification in *E. coli*, the expression cassette from pShuttle was excised using I-Ceu I/PI-Sec I restriction enzymes and cloned into an Ad5F35 expression vector. The recombinant Ad5F35 vector was transfected into human embryonic kidney (HEK) 293 cells and recombinant adenovirus (referred to as AdCMVpoly) was harvested from the transfected cells by successive freeze-thawing cycles.

Example 2

Antigenicity Studies with Recombinant Protein

Immunogenicity Testing of Recombinant Protein by ELISA

Figure 2:
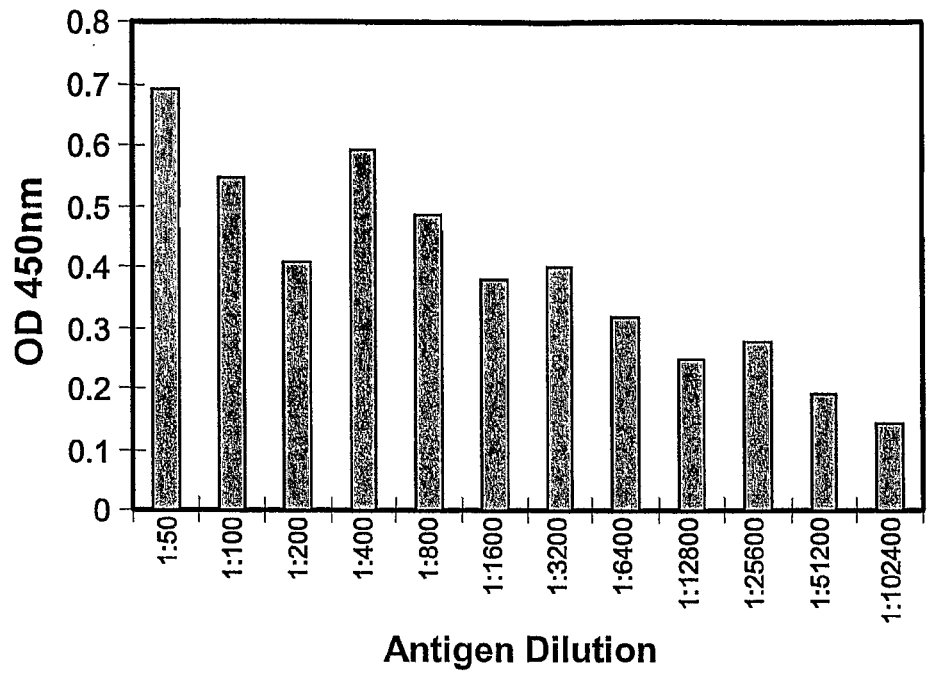

In the first set of experiments, the antigenicity of the recombinant protein using standard ELISA assay was tested. Ninety-six well micro-titre plates were coated with serially diluted (1:50 to 1:102,400) concentrated recombinant protein. These plates were then incubated with anti-gB monoclonal antibody (2F12, 1:8000, Abcam, UK) followed by incubation with secondary antibody (HRP-conjugated anti-mouse Ig, 1:10,000). After extensive washing, the TMB chromogen substrate was added and the OD was read by ELISA reader. Data in Table 3 and in FIG. 2 shows that the recombinant protein is efficiently recognized by the gB-specific monoclonal antibody.

Figure 3:
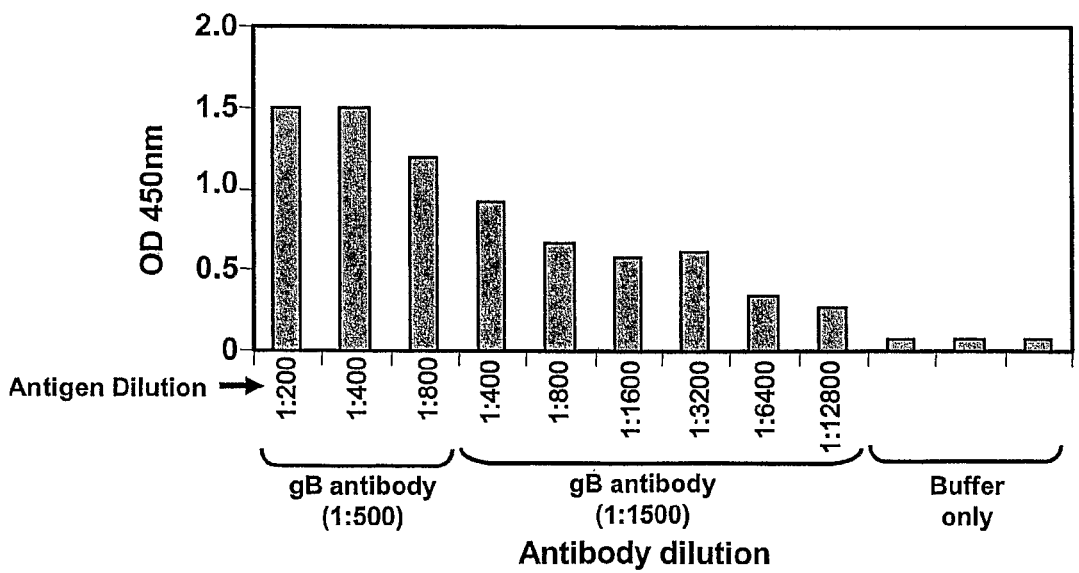

In subsequent experiments, capture ELISA was used to assess the reactivity of the recombinant protein with gB-specific antibody. Ninety-six well micro-titre plates were coated with gB-specific antibody (1-M-12) at dilutions 1:500 (Well 1-3) or 1:1500 (well 4-9) or buffer alone (well 10-12). In each well, recombinant gB-CMV polyepitope protein was added at a dilution of 1:1000 and incubated at 37° C. for 1 h. In the next step, serially diluted rabbit polyclonal antibody specific for gB was added in each well (Wells 1-3: 1:200, 1:400; 1:800 and Wells 4-9: 1:200, 1:400, 1:800, 1:1600, 1:3200, 1:6400 and 1:12800). In wells 9-12, only coating buffer was added. After incubation at 37° C. for 1 h, the plates were washed and secondary antibody (HRP-conjugated anti-rabbit Ig; 1:10,000) was added. Following extensive washing, the TMB chromogen substrate was added and OD was read by ELISA reader. The data in Table 4 and FIG. 3 shows that the gB-specific antibody efficiently captures the recombinant protein.

Immunogenicity Testing of Recombinant HCMV Polyepitope Protein by CTL Assay

Figure 4:
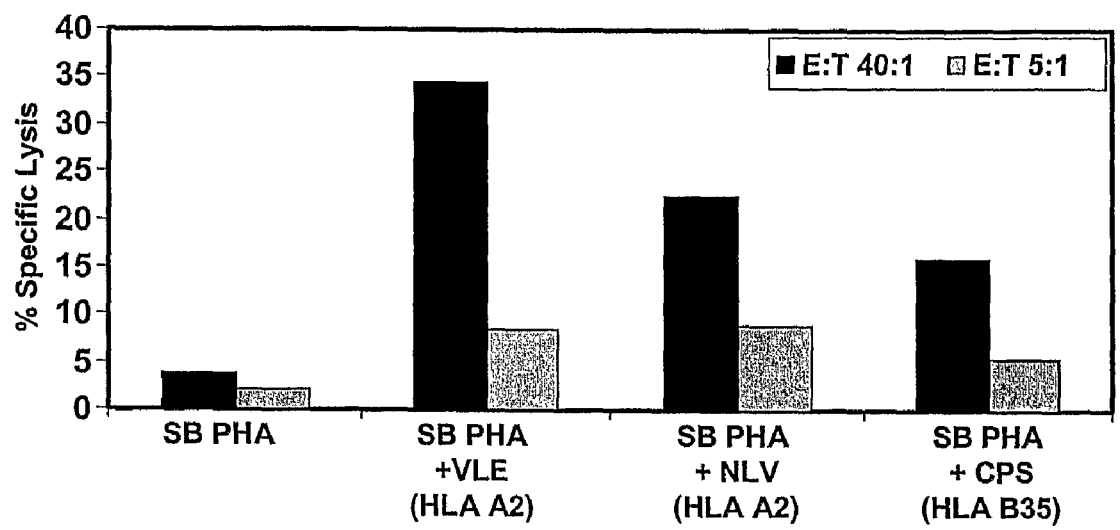
Figure 4:
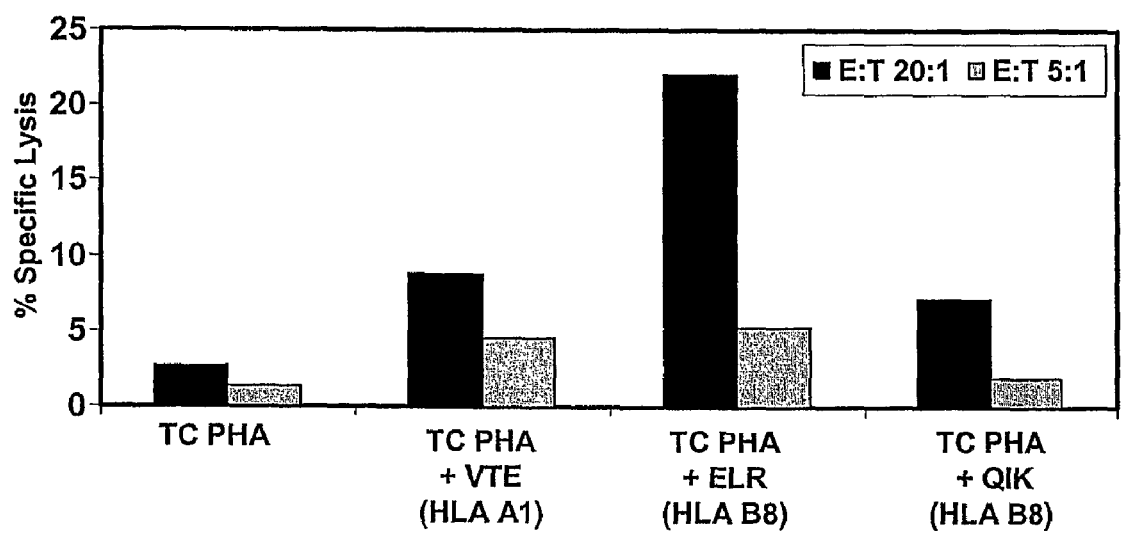

The immunogenicity of the recombinant HCMV polyepitope protein by stimulating human T cells was tested. Briefly, PBMC from healthy seropositive donors were stimulated with the recombinant protein and on day 10 these T cells were tested for a HCMV epitope-specific CTL response. Representative data from two different donors are presented in FIG. 4. Both donors showed activation of multiple epitope-specific CTL activation following incubation with recombinant protein.

Example 3

Recombinant Protein Production in Mammalian Cells

Synthesis of tPA Signal Sequence

A tPA secretion signal sequence or 'Sig' was attached to the gB-CMV-polyepitope construct using the following method. Oligonucleotides TPAS-F and TPAS-R (see Table 3) incorporating a tPA signal sequence with kozak sequences were annealed, extended and the DNA fragment was inserted into pGEM-T (Promega, USA) vector. E. coli DH5α (Invitrogen, USA) was transformed using the ligated products and screened by PCR for the positive clones containing the inserted fragment. The positive colonies were amplified and the plasmids pGEM-tPA were extracted, purified, identified by restriction endonuclease cleavage and the inserted tPA DNA fragment was confirmed by DNA sequencing. The plasmid pGEM-tPA and mammalian expression vector pCEP4 (Invitrogen, USA) were cleaved by Kpn I and Nhe I restriction endonucleases and ligated using T4 DNA ligase. The transformation, amplification and plasmid purification were carried as above, and expression vector pCEP4-tPAS was obtained. By attaching the secretion signal sequence or 'Sig' to the gB-CMV-polyepitope construct, increased activity over the construct without the signal sequence was found.

The Mutagenesis of gB Furin Site

A plasmid pBluscript II-ΔgB which contains a 2100-bp fragment of gB extracellular domain (nucleotide [nt] 81703 to 83805 of the HCMV sequence accession No: NC-001347) was constructed as described above. In order to remove the furin proteolytic processing site, three site-specific point mutations were introduced in the ΔgB by using primers gBmutP1 and gBmutP2, resulting three amino acid changes as follows: $Arg_{433}$ to $Gln_{433}$, $Arg_{435}$ to $Thr_{435}$ and $Arg_{436}$ to $Gln_{436}$.

Removal of Native gB Signal Sequence

In order to remove the gB native signal sequence and facilitate the cloning manipulation, two primers were designed to include both Xba I and Nhe I restriction site in NHEGB-F and Sac II and EcoR I restriction sites in PETGB-R. A 640-bp DNA fragment of gB was amplified by PCR with primers PETGB-R and NHEGB-F using plasmid pBluscript II-ΔgB as template. The purified fragment and plasmid vector pET-26b(+) (Novagen, USA) were cleaved by Xba I and EcoR I and ligated. The transformation, amplification and plasmid purification were carried out as described above and the resulting plasmid pET-26b(+)-αgB was obtained. The inserted fragment was sequence confirmed.

A 1400-bp DNA fragment was cleaved from plasmid pBluscript II-ΔgB by SacII and HindIII and was inserted into the SacII and HindIII sites of vector pET-26b(+)-αgB to produced the plasmid of pET-26b(+)-βgB.

Fusion of Extracellular Domain and Cytoplasmic Domain of gB

For construction of the γgB encoding the extracellular domain (residues $Ser_1$ to $Val_{676}$) and the C-terminal cytoplasmic domain (residues $Lys_{753}$ to $Val_{882}$), the cytoplasmic portion of gB was amplified from AD169 DNA with primers GBTAIL-F and GBTAIL-R, the PCR fragment was purified and cleaved by Hind III and Not I restriction enzymes and inserted into the corresponding sites in plasmid pET-26b(+)-βgB. The transformation, amplification and plasmid purification were carried as previously described and the resulting plasmid pET-26b(+)-γgB was obtained. The inserted cytoplasmic portion of gB was sequence confirmed by DNA sequencing.

His Tagged Polytope2 and Fusion With γgB Synthesis

The plasmid containing the 1320-bp synthetic DNA fragment covering 46 T-cell epitopes was constructed as described above. The primers of CMVP-F (with a terminal Not I site) and Polyhistop 2 (with terminal 6×His tag, stop codon and Xho I site) were used to amplify the 1320 bp DNA fragment by PCR. The PCR fragment was purified and cleaved by NotI and XhoI, and then subcloned into pBluscript II to obtain pBluscript II-Δpoly2. The insert was confirmed by DNA sequencing. The pBluscript II-Δpoly2 was cut with NotI and XhoI and the fragment was subcloned into the plasmid pET-26b(+)-γgB to obtain the plasmid pET-26b(+)-γgB-Δpoly2.

Assembly of the Full Length Mammalian Expression Vector

A 3840 bp DNA fragment encoding gB extracellular domain linked to cytoplasmic domain and CMV polyepitope was cleaved from plasmid pET-26b(+)-βgB-Δpoly2 by Nhe I and Xho I restriction enzymes, purified and ligated with vector pCEP4-tPAS digested by Nhe I and Xho I. The transformation, amplification and plasmid purification were carried out as previously described and the resulting expression plasmid pCEP4-tPAS-γgB-Δpoly2 was obtained. The full sequence of the inserted 3.8 kb fragment was confirmed by DNA sequencing.

Stable Transfection of 293E Cells

Stable transfection of pCEP4-tPAS-γgB-Δpoly2 was achieved by using Effectene (Qaigen) according to the manufacture's instruction. A population of stable transfection was obtained by selection with hygromycin B over a period of 2 weeks. Clonal cell lines were isolated by plating one cell per well in 96-well plates in DMEM containing 10% FCS and 150 μg/ml of hygromycin.

Production of Recombinant Protein

A positive cloned 293E cell line was expanded to grow to confluency in 125-ml flasks in DMEM containing 10% FCS and 150 μg/ml of hygromycin B. The medium was discarded and cells washed with PBS. FreeStyle 293 expression media (Invitrogen, USA) were added to the cells to grow for additional 5 days. After harvest of the supernatant, the medium was cleared of detached cells and debris by centrifugation at 110,000 g. The supernatant was concentrated 100 times by Centricon Plus-80 (Millipore) and stored in −80 C°.

Figure 5:
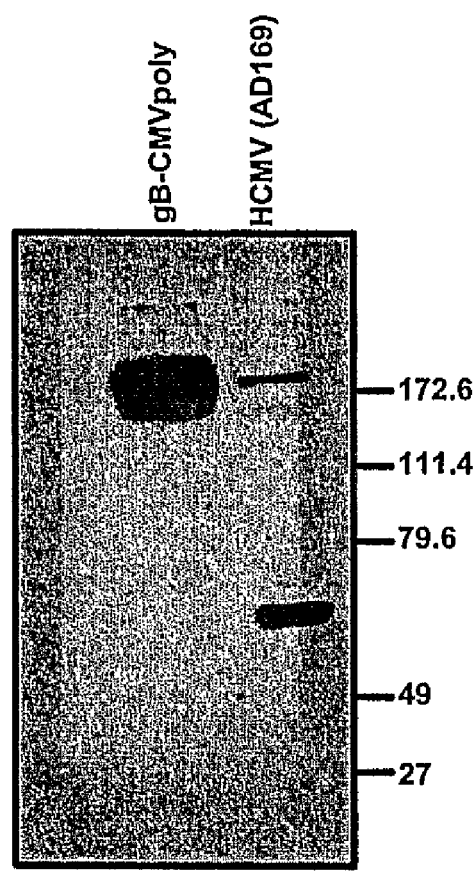

To confirm the integrity of the recombinant protein, concentrated gB-CMV polyepitope protein and HCMV virus extract was resolved on SDS-PAGE gel and then transferred to a nitrocellulose membrane. This membrane was probed with gB-specific monoclonal antibody (2F12, 1:8000, Abcam, UK). Confirmatory data in FIG. 5 shows the expected molecular weight of the recombinant protein.

Example 4

Preclinical Testing of CMV Polyepitope Vaccine

The adenoviral HCMV polyepitope vaccine was used to restimulate a secondary CTL response in vitro from PBMC obtained from healthy HCMV seropositive individuals. The resulting polyclonal cultures were used as effectors against autologous PHA blasts sensitized with HCMV peptide epitopes.

Figure 6:
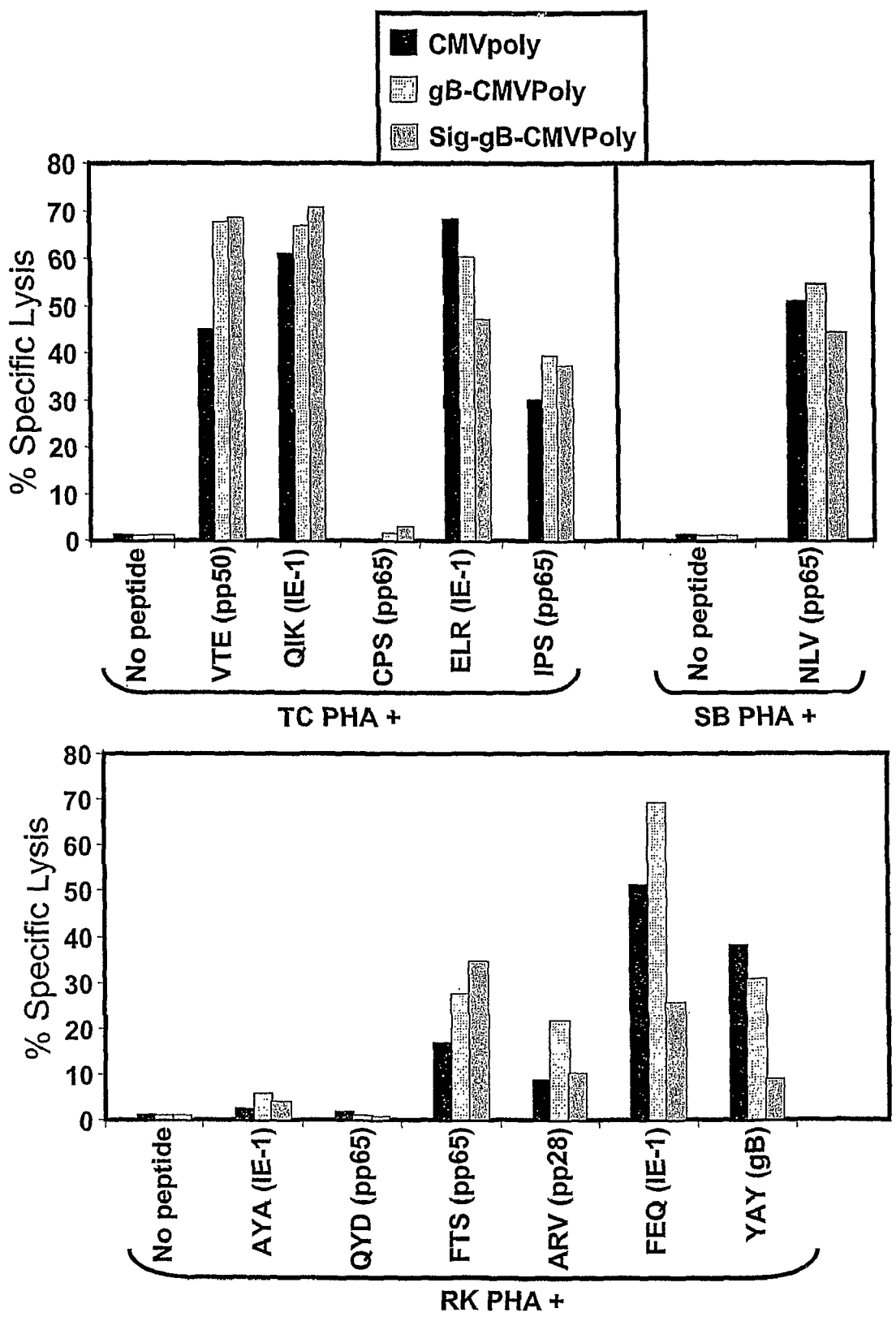

Data in FIG. 6 clearly shows that the HCMV polyepitope was highly efficient in recalling multiple CTL responses which were specific for the epitopes restricted by the HLA alleles expressed by each donor. For instance, the HCMV polyepitope stimulated a strong T cell response to the epitopes VTE (pp50, HLA A1-restricted), ELR and QIK (both I-E-1, HLA B 8-restricted) and IPS (HLA B3 5-restricted, pp65) from donor TC (HLA A1, A11, B8, B35). Another donor who was HLA A2-positive showed strong reactivation of NLV-specific (HLA A2-restricted, pp65) CTL response. Similarly, multiple epitope-specific CTL responses were also detected from other donors.

Significantly, these results demonstrate that the covalent linking of gB to the HCMV polyepitope did not influence endogenous processing and presentation of CTL epitopes.

Example 5

In Vivo Assessment of the Immunogenicity of a HCMV Polyepitope Vaccine

Figure 7:
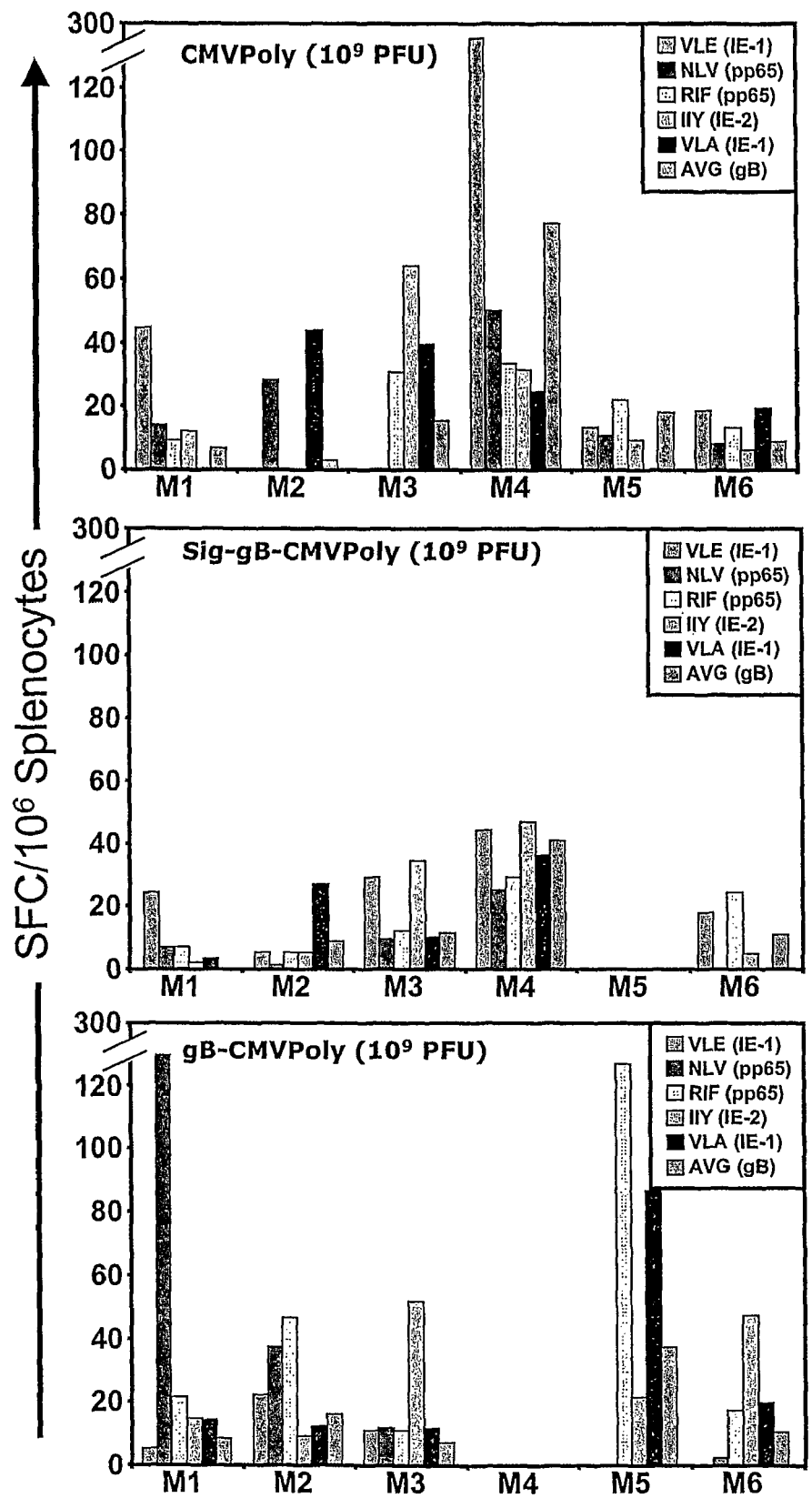

The immunogenicity of each HCMV polyepitope vaccine in vivo was assessed. HEA A2/Kb transgenic mice were immunized intra-peritoneally with recombinant adenovirus HCMV polyepitope vaccine (CMVpoly, gBCMVpoly or Sig-gB-CMVpoly) using standard procedures. A first set of immunizations were carried out using 1×10$^9$ PFU/mouse. Specific T cell reactivity towards HLA-A2-restricted epitopes was assayed on peptide-pulsed targets by enumeration of IFNy-secreting CD8 cells by the ELISPOT method [peptides: NLV (pp65), VLE (IE-1), RIF (pp65), IIY (IE-2), VLA (IE-1) and AVG (gB), all restricted through HLA-A2j]. These studies showed moderate levels of T cell responses to these epitopes following immunization with three different vectors (FIG. 7).

Figure 8:
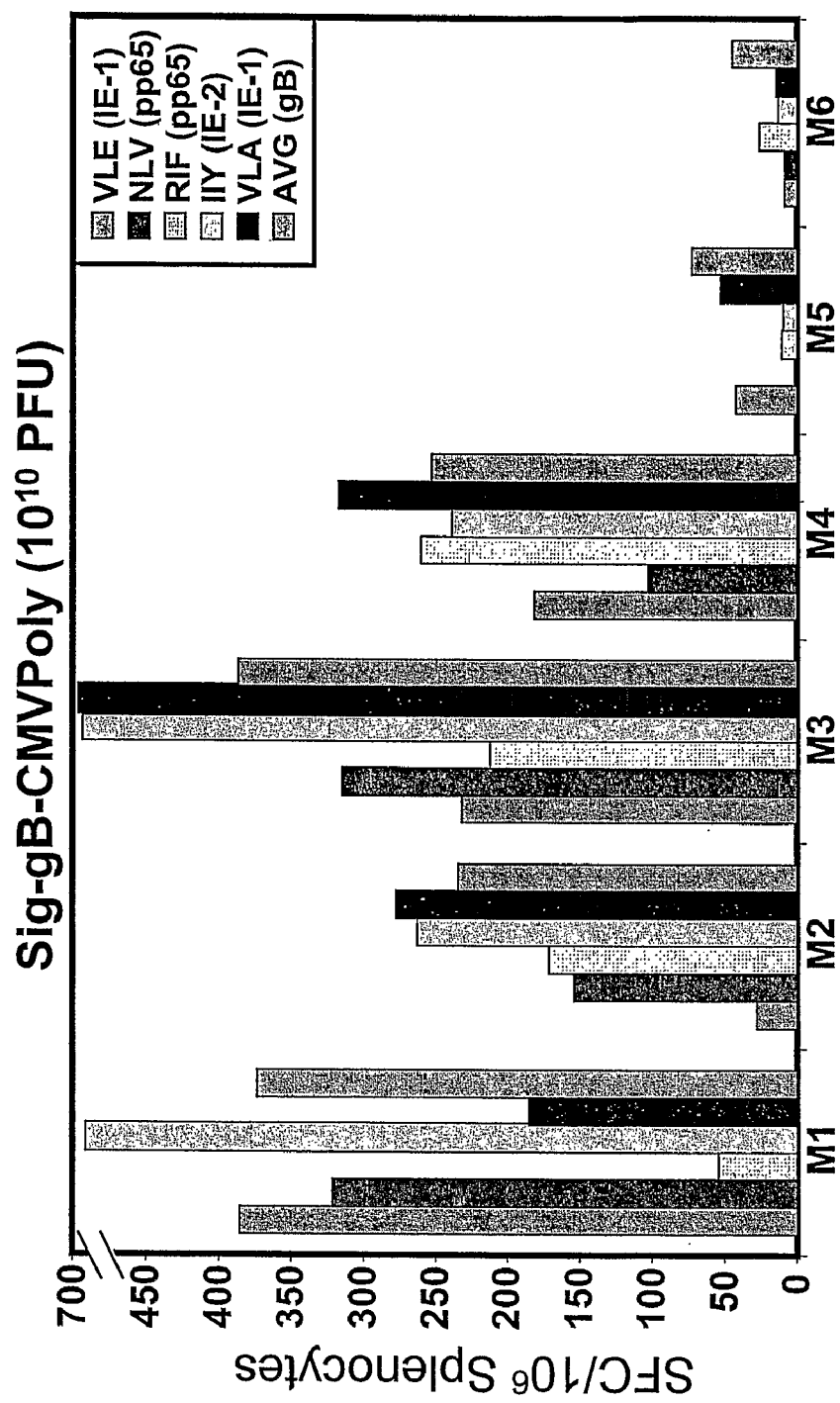

To determine whether the level of T cell responses could be further enhanced by immunizing mice with higher dose of a HCMV polyepitope vaccine, a group of HLA A2/Kb mice were immunized with Sig-gB-CMVpoly at 10$^{10}$ PFU/mouse. Indeed and surprisingly, a single immunization with 10$^{10}$ PFU/mice significantly enhanced the T cell responses (FIG. 8). These responses were ca. 3-10 times higher than those seen in mice immunized with 10$^9$ PFU.

Example 6

Induction of gB-Specific Neutralizing Antibody Response

IE-1/IE-2 HCMV Neutralisation Assay
Reagents

MRC5 fibroblasts; DMEM-0, DMEM-10; 100% MeOH; PBS-5% FCS; mouse anti-CMV monoclonal antibody Cat.# MAB810 1 mg/mL, Ig2a Chemicon International (Silenus); Sheep anti-mouse Ig Fraction affinity isolated Horse Radish Peroxidase conjugated. Product code DAH Cat.# 985033020 2 mL Chemicon Australia Pty Ltd (Silenus) 96 well plates; Peroxidase Block (DakoCytomation, S2001) [0.03% $H_2O_2$ and $NaN_3$ make yourself in PBS]. DAB+ Chromagen (Dakocytomation, K3467)

Neutralisation of HCMV with Mouse Serum and Infection of MRC5 Fibroblasts

Plate MRC5 into 96 well culture plates (2), (should be 80-90% confluent for virus addition). Grow MRC5 cells in DMEM-10, split prior to assay and give 100 μL of a 1×10$^5$ cells/mL suspension in DMEM-10 to wells of a 96 well flat bottom plate to promote an even monolayer of cells. Culture overnight to ensure attachment. Observe culture and when monolayer is 80-90% confluent proceed with assay. Prepare dilutions of sera in a 96 well "U" bottom plate with DMEM-0, remember to change tips between dilutions, ranging from 1/4, 1/8, 1/16 to 1/512 for final range of 1/8, 1/16, 1/32 to 1/1024 leaving 25 μL of the dilution in each well Add 25 μL of HCMV Ad169 too each serum or control well of the 96 well "U" bottom plate.

Incubate the plate at 37° C. for 2 hours.

Aspirate all culture media from the MRC5 culture plate wells. Transfer 25 μL of virus-serum suspension to corresponding wells of the MRC5 culture plate. Infect for 2 hours, rocking the plate gently every 15 min for the first hour, at 37° C. and 7% $CO_2$.

Following incubation aspirate all the inoculum from the wells and wash five times with DMEM-10 then add 200 μL of DMEM-10 to each well and return to culture at 37° C. and 7% $CO_2$ for a further 12 to 16 hours.

IE-1/IE-2 Detection by Horse Radish Peroxidase Staining

Remove all media from culture wells. Wash wells twice with PBS-5%. Fix cells with ice cold 100% MeOH (100 μL 20-30 minutes). Wash cells twice in PBS-5%. Add 1 drop of Peroxidase Block (DalcoCytomation, S2001) and leave for 5-10 minutes. Wash cells twice in PBS-5% at room temperature. Add 25 μL of 1/400 anti-IE-1/IE-2 mAb (freshly diluted in PBS) and incubate for 1-2 hours at room temperature. Wash wells three times with PBS-5% (gently with wash bottle is OK)

Add 50 μL of 1/200 Sheep anti mouse Ig-HRP (freshly diluted in PBS) and incubate overnight/2 hours. Wash wells three times with PBS-5%.

Add 20 μL of DAB+ Substrate Solution too each well and incubate until color develops. Wash wells three times with PBS. Add 100 μL PBS too each well.

Determination of Neutralising Titer

The 50%-inhibition endpoint calculated using the Reed-Munch method was considered the neutralizing titer (NT) NT=reciprocal sera dilution [>50% inhibition]×[(% inhibition greater than 50%-50%)/(% inhibition greater than 50%-% inhibition less than 50%)]

View and count (Positive nuclei in five fields for each of the three replicates only where MRC5 layer is not disrupted) with inverted microscope.

Plot average number of nuclei versus the inverse titre.

Determine the 50% positive nuclei value for the virus alone (no serum) and draw a horizontal line (50% NeutLine).

Determine the 50% neutralizing titer for each of the serum samples by finding the intersection of the serum plot and the 50% NeutLine.

Results

Figure 9:
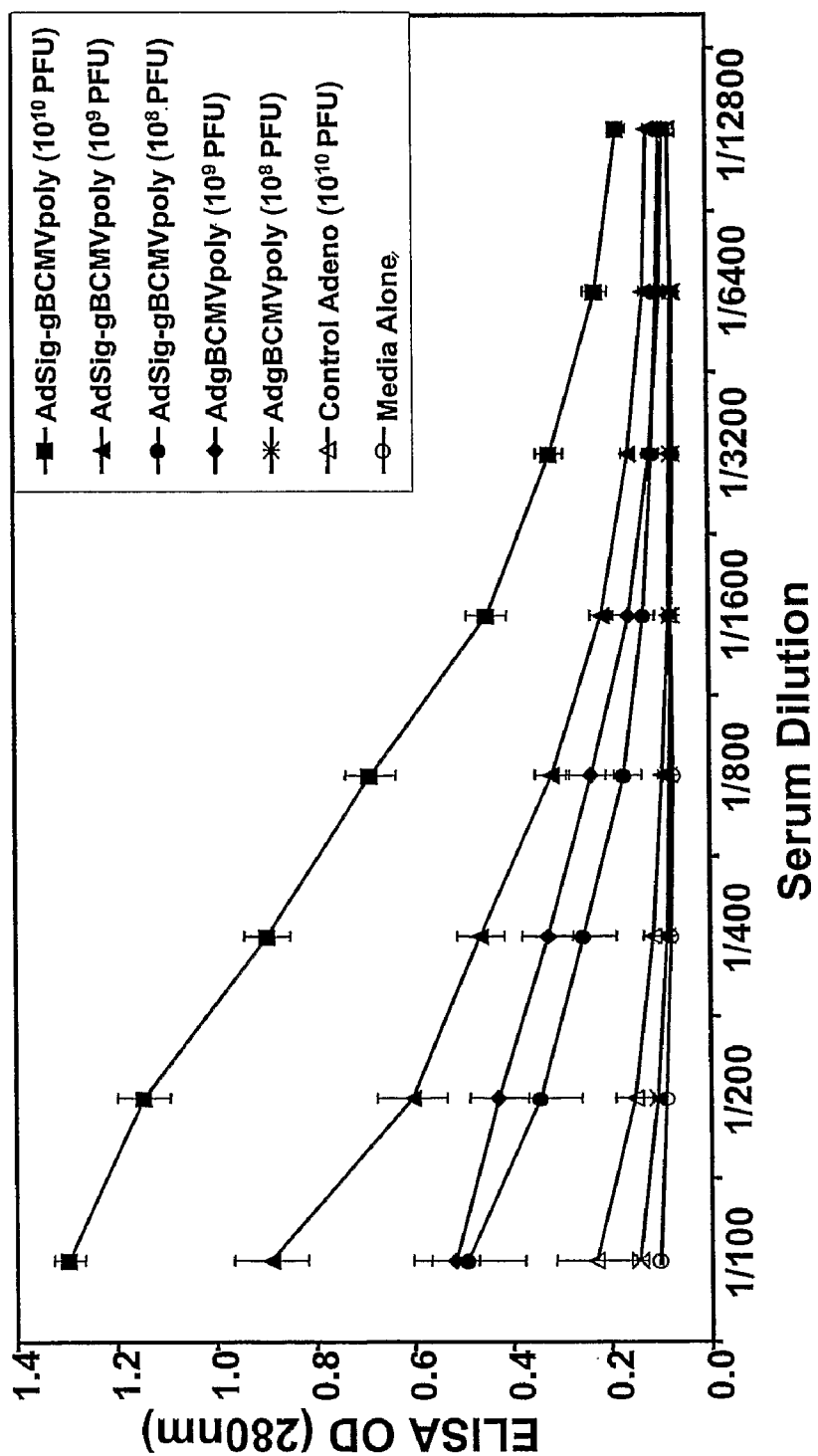

Having previously established the best immunizing dose for the induction of T cell response, the ability of the vaccine comprising the construct Sig-gB-CMVpoly to induce gB-specific antibody response was subsequently assessed. Serum samples from HLA A2/Kb mice immunized with Sig-gB-CMVpoly were collected three weeks after single immunization and tested for gB-specific antibody response by immunoblotting. Serum samples from mock immunized mice were used as a control. FIG. 9 shows the analysis of gB-specific antibody response in serum samples from mice immunized with Adsig-gB-CMVpoly, AdgBCMV poly, control adenovirus or medium alone using ELISA assay.

HCMV virus lysates were resolved on SDS-PAGE gel and then transferred on to nitrocellulose sheets. These sheets were cut into strips and incubated with serum samples from mice or a gB-specific monoclonal antibody (as a positive control). The data in FIG. 10A clearly shows that 4/6 mice immunized with the Sig-gB-CMVpoly construct showed gB-specific antibody response.

Figure 10:
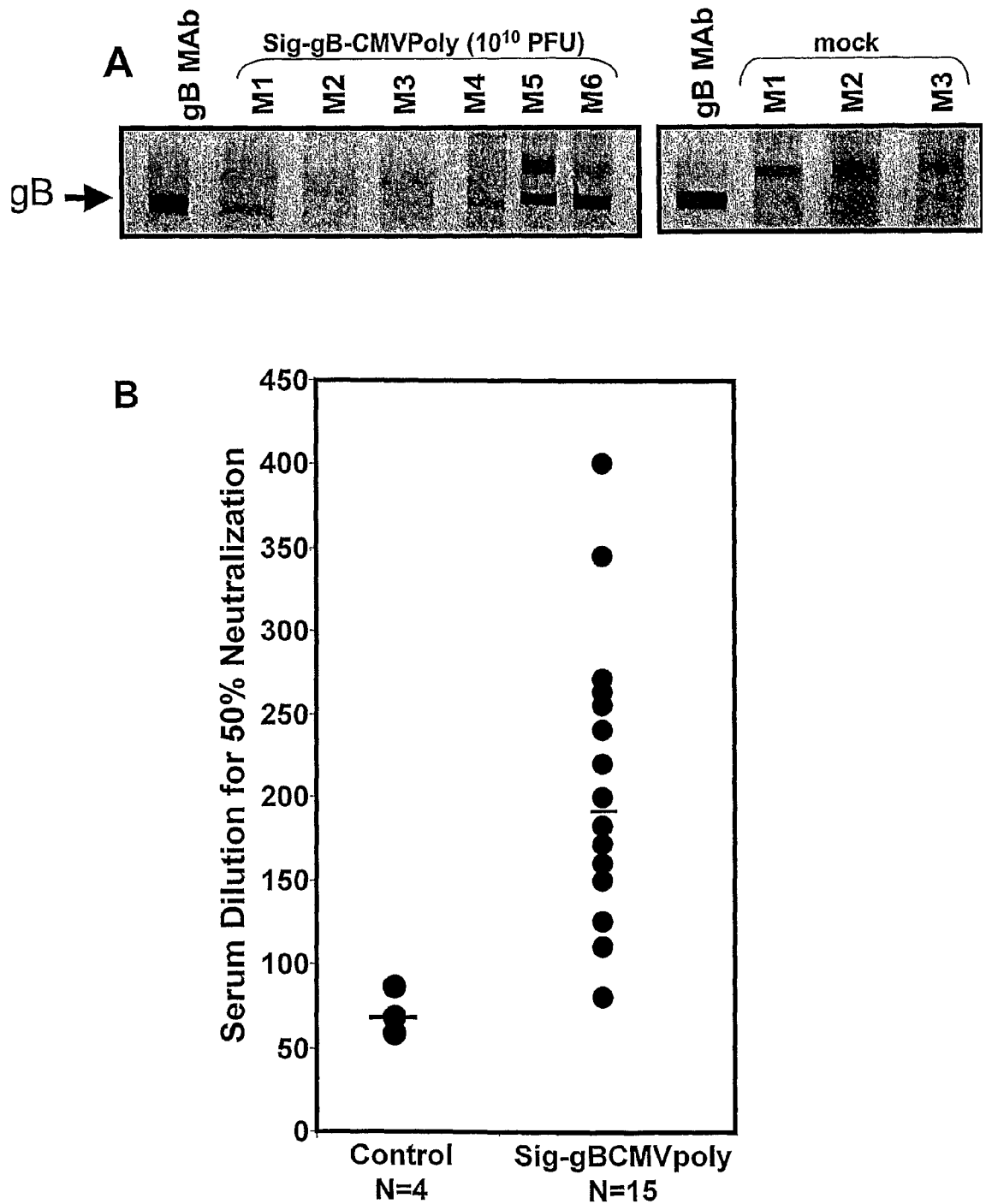

More importantly, as shown in FIG. 10B, serum samples showed significant neutralizing activity in 15 mice immunized with Sig-gB-CMVpoly when compared to 4 control mice (mock immunized with control adenovirus).

These observations clearly show that covalent linking of gB with the polyepitope sequence does not impair the immunogenicity of the individual components of the vaccine. Of particular interest was the ability of the covalently-linked gB to induce neutralizing antibodies which suggests that this chimeric construct is able to maintain the tertiary structure of gB and thus allows the presentation of this protein to the humoral arm of the immune system. It is also imperative to point out that covalent linking of gB does not impede the presentation of CD8+ T cell epitopes from the polyepitope sequence (see FIGS. 7 & 8).

The present inventors further hypothesize that an immunogenic component of a vaccine exclusively for use in transplant patients could be based solely on epitope-related technology, i.e. it is contemplated that constructs without conjugated gB would be sufficient to provide protection against the adverse outcomes of HCMV infection, as protection against disease rather than virus transmission is required.

It will be appreciated that the vaccines comprising the HCMV constructs of the present invention overcome two very important limitations of previous vaccines. Specifically, the new constructs are capable of inducing T cell responses to multiple antigens and are capable of inducing antibody response which shows neutralization of the virus within the same formulation. No vaccine thus far has achieved these two objectives within a single formulation. Such singly formulated vaccines provide substantial commercial advantages over the prior art.

Throughout the specification the aim has been to describe the preferred embodiments of the invention without limiting the invention to any one embodiment or specific collection of features. It will therefore be appreciated by those of skill in the art that, in light of the instant disclosure, various modifications and changes can be made in the particular embodiments exemplified without departing from the scope of the present invention.

All computer programs, algorithms, patent and scientific literature referred to herein is incorporated herein by reference in their entirety.

TABLE 1

List of HCMV epitopes included in the polyepitope

| SEQ ID NO: | Epitope | HLA Restriction | HCMV Antigen |
|---|---|---|---|
| 6 | VTEHDTLLY | HLA A1 | pp50 |
| 7 | NTDFRVLEL | HLA A1 | gB |
| 8 | CVETMCNEY | HLA A1 | IE-1 |
| 9 | VLEETSVML | HLA A2 | IE-1 |
| 10 | NLVPMVATV | HLA A2 | pp65 |
| 11 | RIFAELEGV | HLA A2 | pp65 |
| 12 | IIYTRNHEV | HLA A2 | IE-2 |
| 13 | VLAELVKQI | HLA A2 | IE-1 |
| 14 | AVGGAVASV | HLA A2 | gB |
| 15 | TVRSHCVSK | HLA A3 | pp50 |
| 16 | IMREFNSYK | HLA A3 | gB |
| 17 | GPISHGHVLK | HLA A11 | pp65 |
| 18 | ATVQGQNLK | HLA A11 | pp65 |
| 19 | VYALPLKML | HLA A24 | pp65 |
| 20 | AYAQKIFKIL | HLA A23/A24 | IE-1 |
| 21 | QYDPVAALF | HLA A24 | pp65 |
| 22 | YVKVYLESF | HLA A26 | pp65 |
| 23 | DIYRIFAEL | HLA A26 | pp65 |
| 24 | VFETSGGLVV | HLA A29 | gB |
| 25 | KARDHLAVL | HLA B7 | pp150 |
| 26 | QARLTVSGL | HLA B7 | pp65 |
| 27 | KARAKKDEL | HLA B7/B8 | IE-1 |
| 28 | QIKVRVDMV | HLA B8 | IE-1 |
| 29 | RRRHRQDAL | HLA B8/B27 | pp65 |
| 30 | ARVYEIKCR | HLA B27 | pp28 |
| 31 | KMQVIGDQY | HLA B15 | pp65 |
| 32 | NVRRSWEEL | HLA B7 | pp150 |
| 33 | CPSQEPMSIYVY | HLA B35 | pp65 |
| 34 | KPGKISHIMLDVA | HLA B35 | pp65 |
| 35 | ELRRKMMYM | HLA B8 | IE-1 |
| 36 | IPSINVHHY | HLA B35 | pp65 |
| 37 | FEQPTETPP | HLA B41 | IE-2 |
| 38 | YAYIYTTYL | HLA B41 | gB |
| 39 | QEFFWDANDIY | HLA B44 | pp65 |
| 40 | YEQHKITSY | HLA B44 | pp65 |
| 41 | QEPMSIYVY | HLA B44 | pp65 |
| 42 | SEHPTFTSQY | HLA B44 | pp65 |
| 43 | QAIRETVEL | HLA B57/B58 | pp65 |
| 44 | TRATKMQVI | HLA B57/B58 | pp65 |
| 45 | DALPGPCI | HLA B51 | pp65 |
| 46 | CEDVPSGKL | HLA B40 | pp65 |
| 47 | HERNGFTVL | HLA B40 | pp65 |
| 48 | PTFTSQYRIQGKL | HLA B38 | pp65 |
| 49 | QMWQARLTV | HLA B52 | pp65 |
| 50 | HELLVLVKKAQL | HLA DR11 | gH |
| 51 | DDYSNTHSTRYV | HLA DR7 | gB |

TABLE 2

| Constructs |
|---|
| 1. Kozak sequence ATG gB (amino acid pos 2-700) + CMV polyepitope |
| 2. Kozak sequence ATG gB (amino acid pos 31-700) + CMV polyepitope |
| 3. Kozak sequence ATG CMV polyepitope |
| 4. Kozak sequence ATG gB (amino acid pos 2-700) |
| 5. Kozak sequence ATG gB (amino acid pos 31-700) (no signal sequence) |

TABLE 3

| 1:50 | 1:100 | 1:200 | 1:400 | 1:800 | 1:1600 |
|---|---|---|---|---|---|
| 0.690 | 0.548 | 0.408 | 0.590 | 0.486 | 0.379 |
| 1:3200 | 1:6400 | 1:12800 | 1:25600 | 1:51200 | 1:102400 |
| 0.400 | 0.317 | 0.249 | 0.277 | 0.190 | 0.144 |

TABLE 4

| 1 | 2 | 3 | 4 | 5 | 6 | 7 | 8 | 9 | 10 | 11 | 12 |
|---|---|---|---|---|---|---|---|---|---|---|---|
| 1.494 | 1.491 | 1.193 | 0.923 | 0.669 | 0.583 | 0.613 | 0.345 | 0.278 | 0.074 | 0.073 | 0.080 |

TABLE 5

Oligonucleotides used for construction of CMV vaccine vectors for adenoviral expression

| SEQ ID NO: | OLIGO | DNA SEQUENCE 5' TO 3' |
|---|---|---|
| | | OLIGONUCLEOTIDES FOR gB CONSTRUCTS |
| 52 | pgBSIGF | CGCGGATCCGCCGCCACCATGGAATCCAGGATCTGGTGC |
| 53 | pgBNOSIGF | CGCGGATCCGCCGCCACCATGGCAACTTCTTCTACTCAC |
| 54 | pgBR | CCCAAGCTTTACCTTGTCCTCCACGTACTTTACC |
| | | OLIGONUCLEOTIDES FOR CMV POLYEPITOPE |
| 55 | HCMV 1a | CCCAAGCTTGCCGCCACCATGGTGACCGAGCACGACACCCTGCTGTACAAGCCCGGCAAGATCAGCCACATCATGCTGGACGTGGCCAACAC |
| 56 | pHCMV 1b | CCCAAGCTTGTGACCGAGCACGACACCCTGCTGTACAAGCCCGGCAGATCAGCCACATCATGCTGGACGTGGCCAACAC |
| 57 | pHCMV 1c | ACGCTGGTCTCCTCCAGCACCAGCTCCAGCACGCGGAAGTCGGTGTTGGCCACGTCCAGCATG |
| 58 | pHCMV 2 | GTGGTTCCTGGTGTAGATGATCACGCCCTCCAGCTCGGCGAAGATCCTCACGGTGGCCACCATGGGCACCAGGTTCAGCATCACGCTGGTCTCCTCCAGCAC |
| 59 | pHCMV 3 | GGCCACGGCGCCGCCCACGGCGATCTGCTTCACCAGCTCGGCCAGCACGTACTCGTTGCACATGGTCTCCACGCACACCTCGTGGTTGCGGGTGTAGATGATC |
| 60 | pHCMV 4 | ACGTGGCCGTGGCTGATGGGGCCCTTGTAGCTGTTGAACTCGCGCATGATCTTGCTCACGCAGTGGCTGCGCACGGTCACGCTGGCCACGGCGCCGCCCACG |
| 61 | pHCMV 5 | GGTACACCTTCACGTAGAACAGGGCGGCCACGGGGTCGTACTGCAGGATCTTGAAGATCTTCTGGGCGTAGGCCTTCAGCACGTGGCCGTGGCTGATGGG |
| 62 | pHCMV 6 | GTCGCGGGCCTTCACCACCAGGCCGCCGCTGGTCTCGAACACCAGCTCGGCGAAGATGCGGTAGATGTCGAAGCTCTCCAGGTACACCTTCACGTAGAACAG |
| 63 | pHCMV 7a | AGCAGCTCGTGGATCACCTGCATCTTGGTGGCGCGGGTCAGCTCGTCCTTCTTGGCGCGGGCCTTCAGCACGGCCAGGTGGTCGCGGGCCTTCACCACCAG |
| 64 | pHCMV 7b | TCCACGCGCACCTTGATCTGCACGTAGCGGGTGCTGTGGGTGTTGCTGTAGTCGTCCAGCTGGGCCTTCTTCACCAGCACCAGCAGCTCGTGGATCACCTG |
| 65 | pHCMV 8 | CTCCCAGCTCCTCCTCACGTTCCTGCACTTGATCTCGTACACCCTGGCCAGGGCGTCCTGCCTGTGCCTCCTCCTCACCATGTCCACCCTCACCTTGATCTG |
| 66 | pHCMV 9 | CATCTTGCGGCGCAGCTCCAGGCCGCTCACGGTCAGGCGGGCCTGGTACACGTAGATGCTCATGGGCTCCTGGCTGGGGCACAGCTCCTCCCAGCTGCGGCGCACG |
| 67 | pHCMV 10 | GTGTAGATGTAGGCGTAGGGGGGGGTCTCGGTGGGCTGCTCGAAGTAGTGGTGCACGTTGATGCTGGGGATCATGTACATCATCTTCCTCTTCAGCTCCAGG |
| 68 | pHCMV.11 | CATGGGCTCCTGGTAGCTGGTGATCTTGTGCTGCTCGTAGTAGATGTCGTTGGCGTCCCAGAAGAACTCCTGCAGGTAGGTGGTGTATGTAGGCGTAGGG |
| 69 | pHCMV 12 | CCGCTCGAGAAGCTTCAGCTCCACGGTCTCCCTGATGGCCTGGTACTGGCTGGTGAAGGTGGGGTGCTCGCTGTACACGTAGATGCCATGGGCTCCTGGTAGCTGG |
| 70 | pHCMV-F | CCCAAGCTTGCCGCCACCATGG |
| 71 | pHCMV-FNOATG | CCCAAGCTTGTGACCGAGCACG |
| 72 | pHCMV-R | CCGCTCGAGAAGCTTCAGCTCC |

TABLE 5-continued

Oligonucleotides used for construction of CMV vaccine vectors for adenoviral expression

| SEQ ID NO: | OLIGO | DNA SEQUENCE 5' TO 3' |
|---|---|---|
| | | OLIGONUCLEOTIDES FOR ADDITIONAL CMV EPITOPES |
| 73 | pHCMVPOLYEX TP1 | CCATCGATTGCGAGGACGTGCCCAGCGGCAAGCTGAAGATGCAGGT GATCGGCGACCAGTACGCCACCGTGCAGGGCCAGAACCTGAAGCAC GAGCGC |
| 74 | pHCMVPOLYEX TP2 | GCAGCATCTTCAGGGGCAGGGCGTACACGATGCAGGGGCCGGGCAG GGCGTCCAGCACGGTGAAGCCGTTGCGCTCGTGCTTCAGGTTCTG |
| 75 | pHCMVPOLYEX TP3 | CCGCTCGAGCACGGTCAGGCGGGCCTGCCACATCTGCAGCTTGCCCT GGATGCGGTACTGGCTGGTGAAGGTGGGCAGCATCTTCAGGGGCAGG |
| 76 | pHCMVPOLYEX TPF | CCATCGATTGCGAGGACGTGC |
| 77 | pHCMVPOLYEX TPR | CCGCTCGAGCACGGTCAGGC |

TABLE 6

Oligonucleotide sequences for the construction of expression vectors for protein production in mammalian cells

| SEQ ID NO: | Name | Sequence |
|---|---|---|
| 78 | TPAS-F | 5'-cggggtaccgccgccaccatggatgcaatgaagagagggctctgctgtgctgctgctgtgtggagcagtcttcgtttcgc-3' |
| 79 | TPAS-R | 5'-cccaagcttgctagctagctctggcgcctcttctgaatcgggcatggatttcctggctgggcgaaacgaagactgctccac-3' |
| 80 | GBmutP1 | 5'-gaatatcactcatcagaccacccagagtacgagtgac-3' |
| 81 | GBmutP2 | 5'-gtcactcgtactctgggtggtctgatgagtgatattc-3' |
| 82 | NHEGB-F | 5'-gctctagagctagctctagtacttcccatgcaac-3' |
| 83 | PETGB-R | 5'-ccggaattccgcggctgtgccactgatc-3' |
| 84 | GBTail-F | 5'-cgacaagctttgcacgcagccgctgcag-3' |
| 85 | GBTail-R | 5'-gagtgcggccgcgacgttctcttcttcgtc-3' |
| 86 | CMVP-F | 5'-cgacaagctttgcacgcagccgctgcag-3' |
| 87 | Polyhistop2 | 5'-ccgctcgagtcaatgatgatgatgatgatgcacggtcaggcgggcctgc-3' |

The invention claimed is:

1. An isolated protein comprising:
a Human Cytomegalovirus (HCMV) polyepitope amino acid sequence that comprises a plurality of epitopes, wherein the epitopes are from gH, pp 28, pp 50, pp 65, pp 150, IE-1, and IE-2 HCMV antigens and are capable of eliciting a cytotoxic T-lymphocyte (CTL) response, and one or more HLA class II-restricted CTL epitopes, wherein the epitopes have an amino acid sequence selected from the group consisting of the amino acid sequences set forth in SEQ ID NOS: 6-51, and, wherein the polyepitope comprises each of the amino acid sequences set forth in SEQ ID NOS: 6-51; and
an amino acid sequence of an extracellular domain of HCMV glycoprotein B, or a fragment that comprises at least 75% amino acid sequence identity thereof and comprises one or more B cell epitopes capable of eliciting a neutralizing antibody response.

2. The isolated protein of claim 1, wherein the polyepitope has an amino acid sequence as set forth in SEQ ID NO: 5.

3. An isolated protein comprising:
a Human Cytomegalovirus (HCMV) polyepitope amino acid sequence that comprises a plurality of epitopes, wherein the epitopes are from gH, pp 28, pp 50, pp 65, pp 150, IE-1, and IE-2 HCMV antigens and are capable of eliciting a cytotoxic T-lymphocyte (CTL) response; and
an amino acid sequence of an extracellular domain of HCMV glycoprotein B, or a fragment that comprises at least 75% amino acid sequence identity thereof and comprises one or more B cell epitopes capable of eliciting a neutralizing antibody response, wherein the extracellular domain of HCMV glycoprotein B, or the fragment thereof, includes one or more amino acid substitutions, deletions or additions that remove one or more furin proteolytic cleavage sites normally present in said extracellular domain or said fragment.

4. The isolated protein of claim 3, comprising a plurality of amino acid substitutions which remove said furin proteolytic cleavage site.

5. The isolated protein of claim 4, wherein the plurality of amino acid substitutions are $Arg_{433}$ to $Gln_{433}$, $Arg_{435}$ to $Thr_{435}$ and $Arg_{436}$ to $Gln_{436}$.

6. The isolated protein of claim 5, further comprising a cytoplasmic domain of glycoprotein B contiguous with said extracellular domain or said fragment thereof.

7. The isolated protein of claim 6, further comprising a secretion signal amino acid sequence at the N-terminus of said extracellular domain or said fragment thereof.

8. The isolated protein of claim 7, wherein the secretion signal amino acid sequence is a native gB secretion signal amino acid sequence or a tPA secretion signal amino acid sequence.

9. An isolated protein comprising:
(I) a Human Cytomegalovirus (HCMV) polyepitope amino acid sequence having an amino acid sequence as set forth in SEQ ID NO: 5;
(II) an amino acid sequence of an extracellular domain of HCMV glycoprotein B which comprises one or more B cell epitopes capable of eliciting a neutralizing antibody response, wherein there are one or more amino acid substitutions selected from the group consisting of: $Arg_{433}$ to $Gln_{433}$, $Arg_{435}$ to $Thr_{435}$ and $Arg_{436}$ to $Gln_{436}$;
(III) a cytoplasmic domain of glycoprotein B contiguous with said extracellular domain; and
(IV) a secretion signal amino acid sequence at the N-terminus of said extracellular domain.

10. An isolated nucleic acid encoding a protein, comprising:
(a) a Human Cytomegalovirus (HCMV) polyepitope amino acid sequence that comprises a plurality of epitopes, wherein the epitopes are from gH, pp 28, pp 50, pp 65, pp 150, IE-1, and IE-2 HCMV antigens and are capable of eliciting a cytotoxic T-lymphocyte (CTL) response; and an amino acid sequence of an extracellular domain of HCMV glycoprotein B, or a fragment that comprises at least 75% amino acid sequence identity thereof and comprises one or more B cell epitopes capable of eliciting a neutralizing antibody response; or
(b) protein of claim 9,
wherein said isolated nucleic acid comprises a nucleotide sequence as set forth in SEQ ID NO:3 or SEQ ID NO:4.

* * * * *